United States Patent [19]

Kingston et al.

[11] Patent Number: 5,411,984
[45] Date of Patent: May 2, 1995

[54] WATER SOLUBLE ANALOGS AND PRODRUGS OF TAXOL

[75] Inventors: David G. I. Kingston, Blacksburg, Va.; Jingyu Liang, Nanjing, China

[73] Assignee: Virginia Tech Intellectual Properties, Inc., Blacksburg, Va.

[21] Appl. No.: 963,337

[22] Filed: Oct. 16, 1992

[51] Int. Cl.⁶ .................... A61K 31/335; C07D 305/14
[52] U.S. Cl. .................................. 514/449; 549/510; 549/511
[58] Field of Search ................. 549/510, 511; 514/449

[56] References Cited

U.S. PATENT DOCUMENTS

| | | | |
|---|---|---|---|
| 4,814,470 | 3/1989 | Colin et al. | 514/449 |
| 4,857,653 | 8/1989 | Colin et al. | 549/511 |
| 4,942,184 | 7/1990 | Haugwitz et al. | 514/449 |
| 4,960,790 | 10/1990 | Stella et al. | 514/449 |
| 5,015,744 | 5/1991 | Holton | 549/510 |
| 5,059,699 | 10/1991 | Kingston et al. | 549/511 |

FOREIGN PATENT DOCUMENTS 0400971 12/1990 European Pat. Off. .

OTHER PUBLICATIONS

Kingston et al., "The Chemistry of Taxol, A Clinically Useful Anti-Cancer Agent", J. Nat. Prod., 53, 1–12 (1990).
Deutsch et al., "Synthesis of Congeners and Prodrugs 3. Water–Soluble Prodrugs of Taxol With Potent Anti-tumor Activity", J. Med. Chem., 32, 78–792 (1989).
Mangatal et al., "Application of the Vicinal Oxyamination Reaction with Asymmetric Induction to the Hemisynthesis of Taxol and Analogues", Tetrahedron, 45, 4177–4190 (1989).
Zhao et al., "Modified Taxols, 6. Preparation of Water–Soluble Prodrugs of Taxol", J. Nat. Prod., 54, 1607–1611 (1991).
Magri et al., J. Org. Chem., 51, 30–39, (1986).
Mathew et al., "Synthesis and Evaluation of Some Water–Soluble Prodrugs and Derivatives of Taxol with Antitumor Activity", J. Med. Chem., 35, 145–151 (1992).
Swindell et al., "Biologically Active Taxol Analogs With Deleted A-Ring Side-Chain Substituents and Variable C-2′ Configurations", J. Med. Chem., 34, 1176–1184 (1991).
Monsarrat et al., "Isolation and Identification of Three Major Metabolites of Taxol and Rat Bile", Drug Metabolism and Dispositions, 18, 895–901 (1990).
McGuire et al., "Taxol: A Unique Antineoplastic Agent with Significant Activity in Advanced Ovarian Epithelial Neoplasms", Ann. Int. Med., 111, 273–279 (1989).
Holmes et al., "Phase II Trial of Taxol, an Active Drug in the Treatment of Metastatic Breast Cancer", J. Nat. Can. Inst., 24, 1791–1805 (1991).
Rowinsky et al., "Taxol: Twenty Years Later, the Story Unfolds", J. Nat. Can. Inst., 24, 1778–1781 (1991).
Gueritte–Voegelein et al., "Chemical Studies of 10–Deacetyl Baccatin III. Hemisynthesis of Taxol Derivatives", Tetrahedron, 42, 4451–4460 (1986).
Kingston, "The Chemistry of Taxol", Pharmac. Ther., 52, 1–34 (1991).
Ringel et al., "Studies with RP 56976 (Taxotere): A Semisynthetic Analogue of Taxol", J. Nat. Can., Inst., 4, 288–291 (1991).
Gueritte–Voegelein et al., "Relationships Between the Structure of Taxol Analogues and Their Antimitotic Activity", J. Med. Chem. 34, 992–998 (1991).

*Primary Examiner*—Bernard Dentz
*Assistant Examiner*—Ba K. Trinh
*Attorney, Agent, or Firm*—Popham, Haik, Schnobrich & Kaufman, Ltd.

[57] ABSTRACT

Substituted 2′-benzoyl and 2′, 7-dibenzoyl taxol derivatives are synthesized which have improved water solubility and stability while maintaining bioactivity. In a preferred embodiment, taxol 2′,7-di(sodium 1,2-benzenedicarboxylate) is synthesized by reacting taxol with phthalic anhydride, and subsequently neutralizing the resulting acid by an ion exchange resin. Taxol 2′-(sodium 1,4-benzenedicarboxylate) is prepared by reacting the monobenzyl ester of 1,4-benzene dicarboxylic acid with taxol in the presence of dicyclohexyl carbodiimide and dimethylaminopyridine, hydrogenolysing the resulting ester to remove the benzyl group, and neutralizing with ion exchange resin. Other taxol prodrugs are prepared by modifications of these routes. In a preferred embodiment, the compounds prepared have improved water-solubility as compared with taxol and demonstrate activity in the M109 mouse bioassay system.

47 Claims, 7 Drawing Sheets

WATER SOLUBLE ANALOGS AND PRODRUGS OF TAXOL

FIELD OF THE INVENTION

The present invention relates to water soluble aroyl derivatives of taxol with anti-neoplastic activity, and relates more particularly to 2'-0-benzoyl and 2',7-0-dibenzoyl derivatives of taxol which carry additional solubilizing groups on the benzoyl moiety.

BACKGROUND OF THE INVENTION

Taxol is a naturally occurring diterpenoid which has demonstrated great potential as an anti-cancer drug. Taxol was first isolated and its structure reported by Wani, et al., in "Plant Anti-Tumor Agents. VI. The Isolation and Structure of Taxol. A Novel Anti-Leukemic And Anti-Tumor Agent From *Taxus Brevifolia*," J. Am. Chem. Soc., 1971, 93, 2325. Taxol is found in the stem bark of the Western Yew, *Taxus brevifolia*, as well as in *T. baccata* and *T. cuspidata*.

The biological activity of taxol is related to its effect on cell division. Taxol promotes formation of microtubules that form the mitotic spindle during cell division. However, taxol prevents depolymerization of the tubulin forming the microtubules of the mitotic spindle, which is essential for cell division to take place. Thus, taxol causes cell division to stop. Taxol's mechanism is unique since it promotes the formation of tubulin polymers, whereas other anti-cancer drugs, such as vinblastine and colchicine, prevent microtubule formation.

Extensive testing of taxol has been a slow process because the drug is in short supply, and it has not yet been successfully synthesized. However, studies have been completed by McGuire et al., that demonstrate that taxol shows excellent clinical activity against drug-refractory ovarian cancer. See "Taxol: A Unique Antineoplastic Agent With Significant Activity In Advanced Ovarian Epithelial Neoplasms," *Ann. Int, Med.*, 111, 273–279 (1989). Another study by Holmes, et al., demonstrates that taxol is an active drug in the treatment of metastatic breast cancer. See "Phase II Trial of Taxol, An Active Drug In The Treatment Of Metastatic Breast Cancer," *J. Natl. Cancer Inst.*, 83, 1797–1805 (1991). All references cited herein are incorporated by reference as if reproduced in full below.

In both of these studies, taxol had to be administered by 24-hour infusions to avoid problems from allergic reactions due to the polyethoxylated castor oil diluent (known by the tradename Cremophor EL) used in the formulation of taxol. The diluent is required because of the low water solubility of taxol. If a prolonged infusion and premedication with antiallergic drugs is not used, severe allergic reactions and even death have resulted. See Weiss et al., "Hypersensitivity Reactions From Taxol, "*J. Clin. Oncol.*, 8, 1263–1268 (1990). For these reasons, the preparation of derivatives of taxol which are more water soluble than taxol, and which retain at least some of the antineoplastic activity of the parent drug is an important objective.

The biological activity of taxols substituted at the C-2' and C-7 positions in order to make them more water soluble has been reported See Magri and Kingston, "Modified Taxols, 4. Synthesis And Biological Activity Of Taxols Modified In The Side Chain," *J. Nat. Prod.*, 51, 298–306 (1988). A 2'-(t-butyldimethylsilyl) taxol was synthesized and found to be essentially inactive; this was taken as an indication of the need for a free hydroxyl group at the 2' position of the taxol side chain for biological activity. Further, acyl substitutes at the 2' position in 2'-acetyltaxol and 2',7-diacetyltaxol were readily hydrolyzed under in Vivo conditions, and both acetylated compounds showed activity in a cell culture bioassay. The lability of the acyl substitutes at the 2' position suggested that 2'-acetyltaxols could serve as pro-drug forms of taxol (generally, a prodrug is a compound which exhibits pharmacologic activity after biotransformation).

Two taxols with increased water solubility were prepared, 2'-(β-alanyl)-taxol (1) and 2'-succinyltaxol (2):

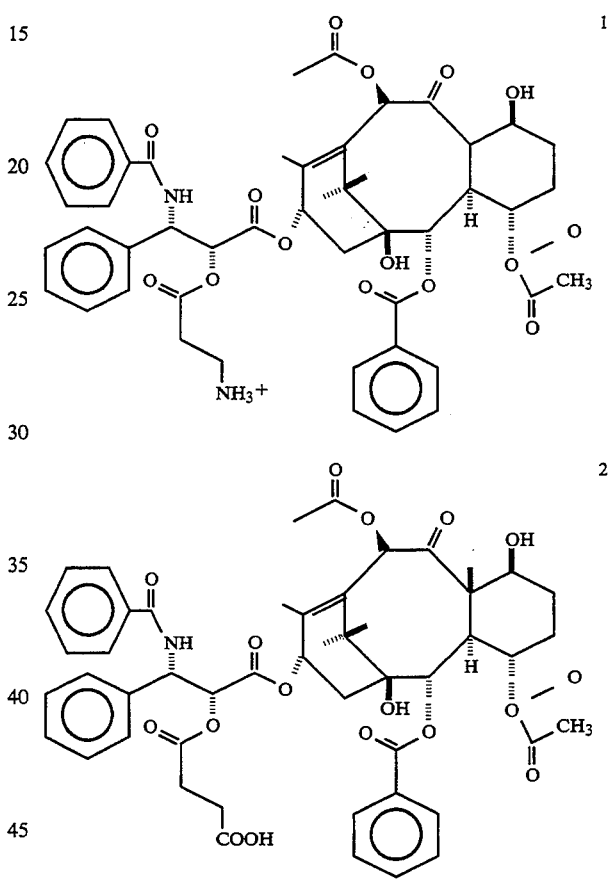

The 2'-(β-alanyl)taxol was found to be active in vivo and in vitro, but was unstable. The 2'-succinyltaxol, prepared by the treatment of taxol with succinic anhydride, had a diminished P-388 in vivo activity as compared with taxol. Thus, research efforts were concentrated on further alterations to taxol and to the known derivatives of taxol (e.g., further derivatives of 2'-succinyl taxol).

Deutsch et al., in "Synthesis of Congeners And Prodrugs. 3. Water-Soluble Prodrugs Of Taxol With Potent Antitumor Activity," *J. Med. Chem.*, 32, 788–792 (1989), reported that salts of 2'-succinyltaxol and 2'-glutaryltaxol had improved antitumor activities when compared to the free acids. Since these researchers believed that salts prepared with different counter ions often have substantially different properties, a variety of 2' substituted taxol salts were synthesized and tested. Triethanolamine and N-methylglucamine salts of the 2' substituted taxol derivatives showed greatly improved aqueous solubility and had more activity than sodium salts. Further, a series of 2'-glutaryltaxol salts were found to have higher activity than their 2'-succinyltaxol analogs. In particular, the taxol salt resulting from the coupling of 2'-glutaryltaxol with 3-(dimethylamino)-1-propylamine using N,N'-carbonyldiimidazole (CDI) demonstrated good solubility and bioactivity.

Mathew et al., in "Synthesis And Evaluation Of Some Water-Soluble Prodrugs And Derivatives Of Taxol With Antitumor Activity," *J. Med. Chem.*, 35, 145–151 (1992), reported the synthesis and evaluation of some 2'-and 7-amino derivatives of taxol. The methane sulfonic acid salts of both 2'- and 7-amino acid esters of taxol showed improved solubility ranging from 2 to greater than 10 mg/mL. The derivatives 2'-(N,N-dimethylglycyl) taxol and 2'-[3-(N,N-dimethylamino)propionyl]taxol inhibited proliferation of B16 melanoma cells to an extent similar to that of taxol, while other derivatives were about 50% as cytotoxic.

Zhao and Kingston, in "Modified Taxols 6. Preparation of Water-Soluble Prodrugs of Taxol," *J. Nat. Prod.*, 54, 1606–1611 (1991), showed that 2'-[(3-sulfo-1-oxopropyl)oxy]taxol sodium salt, 2'-([4-((2-sulfoethyl)amino)-1,4-dioxobutyl]oxy)taxol sodium salt, and 2'-([4-((3-sulfopropyl)amino-1,4-dioxobutyl]oxy)taxol sodium salt have improved water-solubility as compared with taxol and are active as antineoplastic agents in mice. In addition to the above compounds, Kingston and Zhao in U.S. Pat. No. 5,059,699 also describe the synthesis of 2'-γ-aminobutyryltaxol formate and ethylene glycol derivatives of 2'-succinyltaxol.

Taxol prodrugs prepared to date include taxol derivatives having an added aliphatic carboxylic acid moiety. These compounds, however, are readily hydrolysed back to taxol by mild base, and are thus relatively unstable compounds. U.S. Pat. No. 4,942,184 describes the synthesis of several 2' aliphatic carboxylic acid derivatives of taxol. U.S. Pat. No. 4,942,184 also discloses the synthesis of 2'-orthocarboxybenzoyl taxol, although the 2' glutarate series of taxol derivatives are reported to be preferred. It is believed that short aliphatic 2' substituents (e.g., succinyl and glutaryl) were preferred for coupling taxol to solubilizing functionalities, since longer aliphatic or cyclic substituents would lower water solubility. Thus efforts have been concentrated on substituting functional groups on taxol having water solubilizing groups coupled to taxol through short aliphatic chains (e.g. $C_{3-5}$).

Taxol, taxol congeners, and prodrugs of both are difficult to synthesize due to the large size and complexity of these compounds, the presence of multiple reactive sites, and the presence of many stereospecific sites. Thus, compared to the importance of these compounds, relatively few taxol congeners and prodrugs have been prepared. Nevertheless, for ease of administration and to minimize allergic side effects, it is desirable to synthesize taxol and taxol congener prodrug formulations that are soluble and stable for several hours or more in aqueous solution, but that can be hydrolysed readily in vivo to yield taxol or an antineoplastic taxol congener.

Thus, there remains a need for taxol derivatives which are soluble and stable in water and exhibit antineoplastic activity. There is a corresponding need to develop synthetic routes to preparing prodrugs of taxol and taxol congeners that exhibit these properties.

OBJECTS OF THE INVENTION

Thus, it is a primary object of this invention to produce prodrug forms of taxol and taxol congeners for the treatment of cancer.

It is a further object to produce water-soluble derivatives of taxol and taxol congeners which are stable in aqueous solution.

It is another object of this invention to prepare intermediates which can be directly converted to prodrug forms of taxol and taxol congeners.

SUMMARY OF THE INVENTION

These and other objects of the present invention are achieved in the present invention, which relates to the production of water soluble taxol derivatives as water soluble 2-0-aroyl (or 2-0-aryloyl) substituted derivatives of taxol or of taxol congeners as described in greater detail below. It has been surprisingly discovered that taxol prodrugs having substituted 0-benzoyls at the 2' position or 2' and 7 positions, are soluble and stable in aqueous solution for more than 24 hours; thus, in a preferred embodiment, the present invention produces prodrugs that can be stored in their diluted form while maintaining their therapeutic value.

In a preferred embodiment, the hydroxyl group at the C-2' position on the C-13 side chain of taxol or a taxol congener is replaced by a substituted 0-benzoyl group. At least one of the substituents on the phenyl ring of the benzoyl contains a functional group which serves to increase the water solubility of the derivative, or contains a group which can be readily converted to a functional group which serves to increase the water solubility of the derivative.

In another embodiment of the present invention, compounds are produced having the general structure shown below:

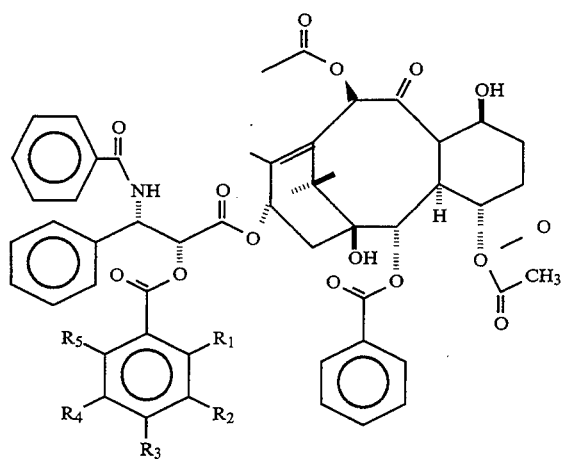

wherein $R_1$, $R_2$, $R_3$, $R_4$, and $R_5$ ($R_1$–$R_5$ or $R_{1-5}$) are substituents which can be the same or different, and which can be hydrogen, alkyl s, aryls, esters, amines, sulfonates, carboxylates ($COOX^+$; where $X^+$ is a counterion, such as but not limited to H, $Na^+$, and $K^+$), substituents containing ammonio ions, substituted alkyls and substituted aryls, provided that (1) $R_{1-5}$ can not simultaneously be H, (2) when $R_{1-4}$ are H, $R_5$ is not $COO^-X^+$, and (3) when $R_{2-5}$ are H, $R_1$ is not $COO^-X^+$. In a preferred embodiment, at least one of $R_{1-5}$ is either an alkali metal carboxylate or sulfonate (e.g., —COONa or —SO$_3$K).

In a further embodiment of the present invention, compounds are produced having the general structure:

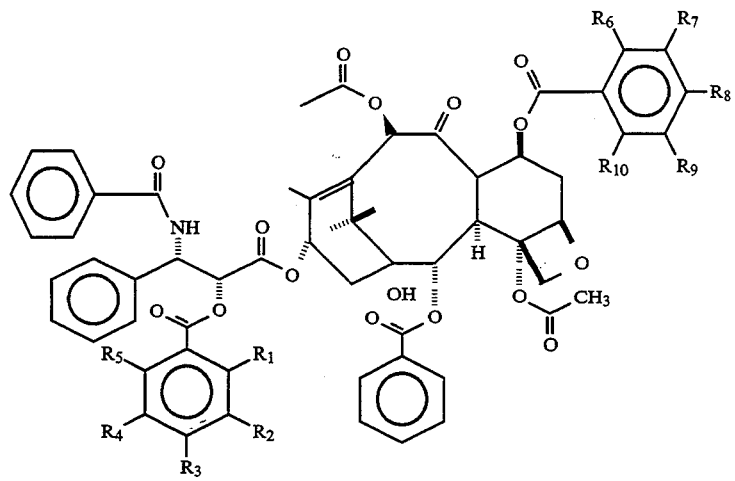

wherein $R_1$–$R_{10}$ are substituents which can be the same or different, and can be hydrogen, alkyls, aryls, esters, amines, sulfonates, carboxylates, substituents containing ammonio ions, substituted alkyls and substituted aryls. In a preferred embodiment, at least one of $R_1$–$R_{10}$ is either an alkali metal carboxylate or sulfonate. The preferred prodrug forms of taxol and taxol congeners of the present invention exhibit the highly desirable properties of water solubility, chemical stability in aqueous solution, and antineoplastic activity.

DEFINITIONS

Figure 1:
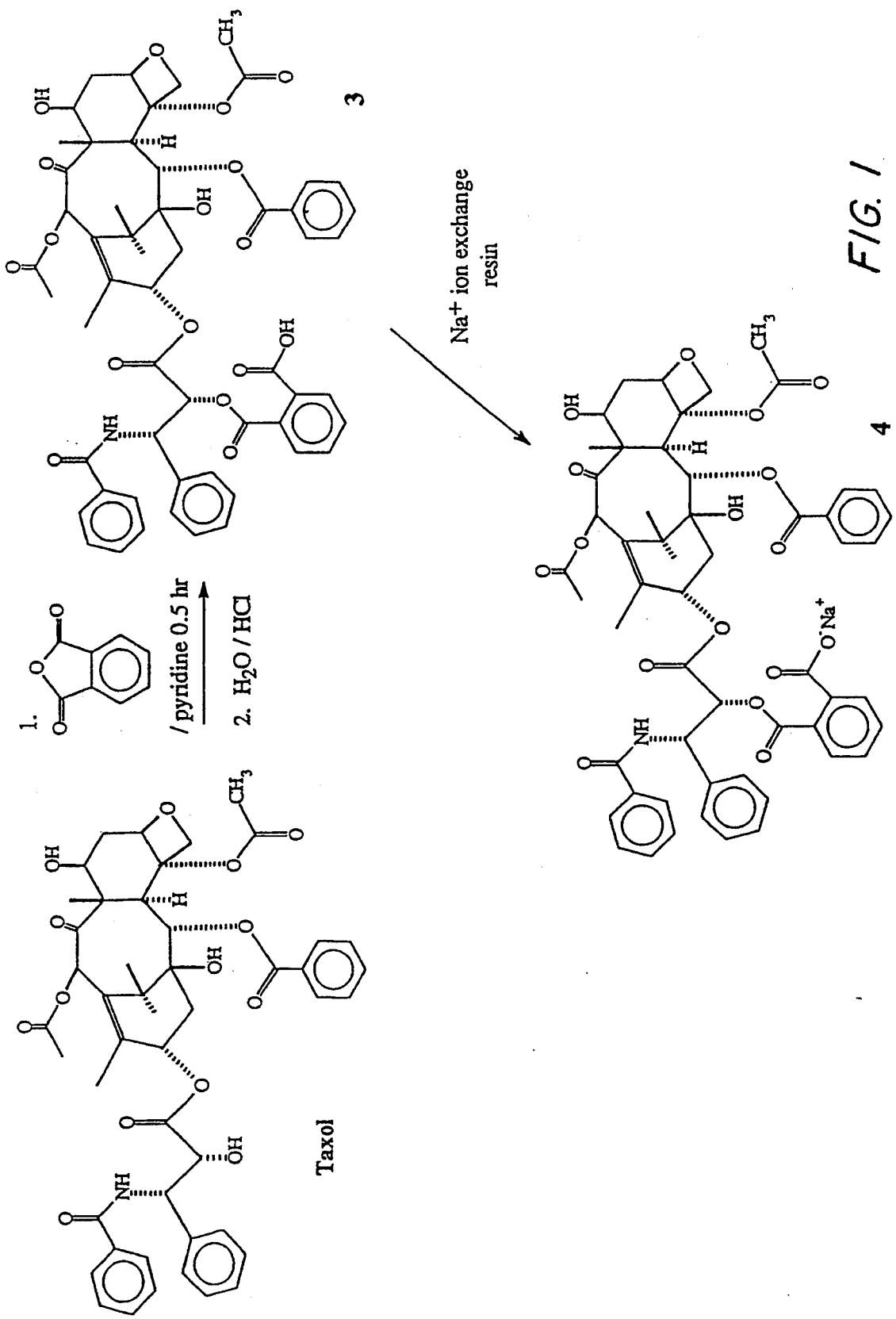
FIG. 1 illustrates the synthesis of taxol 2'-(sodium-1,2-benzenedicarboxylate) from taxol via reaction with phthalic anhydride in the presence of pyridine followed by sodium ion exchange.

Unless clearly indicated by context or statement to the contrary, the terms used herein have the meanings as conventionally used in the chemical arts, and definitions incorporate those used in standard texts, such as Grant & Hackh's Chemical Dictionary, 5th edition, McGraw-Hill, 1987.

For ease in describing the present invention, taxol congeners are generally defined as those compounds having antineoplastic activity, or which are intermediates useful for making compounds having antineoplastic activity, comprising the taxane skeleton shown below (Formula I):

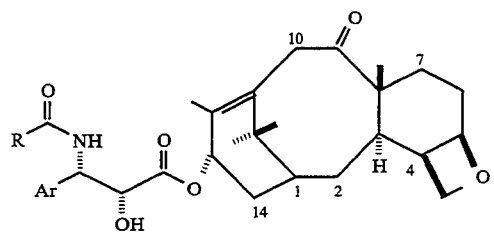

wherein Ar is an aryl and R is an alkyl, alkenyl, alkynyl, aryl, alkoxy, ester, amido, alkyloyl, alkenyloyl, alkynyloyl, or an aroyl, and the rings of the taxane skeleton carry substitutents including, but not limited to, substituents at the C-1, C-2, C-4, C-7, and C-10 positions such as but not limited to hydroxy, alkoxy, and esters.

The term ammonio refers to NH$_4$+ or refers to NH$_4$+ wherein one or more H atoms can be substituted by substituents including an alkyl or aryl. In this invention, ammonio ions may be counter ions to taxol compounds or may be covalently attached to the taxol compounds.

Suitable cations include but are not limited to the alkali metal cations (e.g. Na+ and K+) and the ammonio cations. Suitable cations also include ions (e.g. hydrogen) that are able to exchange with alkali ions, thus resulting in the alkali-salt, prodrug forms of taxol and taxol congeners.

The term alkyl refers to straight-chain or branched hydrocarbons. In some preferable embodiments, alkyl refers to the lower alkyls containing from one to six carbon atoms in the principal chain and up to 10 carbon atoms; the lower alkyls may be straight or branched chain and by way of nonlimiting example include methyl, ethyl, propyl, isopropyl, butyl, isobutyl, tert-butyl, and the like.

The term alkyl also refers to the substituted alkyl groups including, but not limited to, the alkyl groups discussed above which have as substituents halo, e.g., chloro, bromo; nitro; sulfate; sulfonyloxy; carboxy; carboxylate, e.g., $COO^-$; phosphate, e.g., $OP(O)(OH)_2$, $OP(O)(OR)(OH)$, and the like; carbo-lower-alkoxy, e.g., carbomethoxy, carbethoxy; amino; mono- and di-lower-alkylamino, e.g., methylamino, dimethylamino, carboxamide; sulfonamide; diethylamino, methylethylamino; amide; lower-alkoxy, e.g., methoxy, ethoxy; lower-alkanoyloxy, e.g., acetoxy; alkenyl, alkynyl; aryl; aryloxy; and combination of these, e.g., alkylbenzenesulfonates.

In a preferred embodiment the substituted alkyl will be diethylaminoethylamino carbonyl and its hydrochloride derivative.

The term aryl has the meaning known in the chemical arts, and aryl also refers to substituted aryls having the same substituents discussed above for the substituted alkyls and also includes, but is not limited to, aryls having the substituents, lower alkyl, e.g. methyl, ethyl, butyl, etc.

DETAILED DESCRIPTION OF THE INVENTION

Taxol was obtained from BRISTOL-MYERS SQUIBB COMPANY. $^1$H-NMR and $^{13}$C-NMR spectra were made with a Bruker 270SY 270 MHz spectrometer; 2D-NMR were obtained using a Bruker WP 200 200 MHz spectrometer. Chemical shifts are all recorded in parts per million (ppm) downfield from TMS in $^1$H-NMR, and $^{13}$C-NMR chemical shifts are based on chloroform's shift at 77.0 pm or on the TMS shift at 0 ppm. Samples were generally recorded while in CDCl$_3$ or CD$_3$OD at ambient temperature. Mass spectra were obtained using a Finnegan-MAT 112 gas chromatograph-mass spectrometer and VG 7070 HF mass spectrometer equipped with data system, FAB source, and EI/CI source. HPLC was carried out on an apparatus consisting of a Waters M6000 pump, a Rheodyne injection valve, a Waters Radial-Pak RLM-100 RP-8 column, and a Waters 440 UV detector. Melting points were taken on a Thermolyne hot bench and are uncorrected. Optical rotations were determined on a Perkin-Elmer 141 Polarimeter. Preparative TLC was carried out on silica gel GF(Uniplate, 20 ×20 cm, 0.5 mm). UV spectra were recorded on a Perkin Elmer 330 spectrophotometer. IR spectra were recorded as KBr pellets on a Perkin Elmer 283B infrared spectrophotometer.

With reference to FIG. 1, the known compound taxol 2'-(sodium 1,2 benzenedicarboxylate) (4) can be prepared by condensing benzene 1,2-dicarboxylic anhydride (phthalic anhydride) with taxol to yield taxol 2'-(hydrogen-1,2-benzenedicarboxylate), (3), which is then converted to taxol 2'-(sodium 1,2-benzenedicarboxylate) (4) by treatment with ion exchange resin in the sodium form.

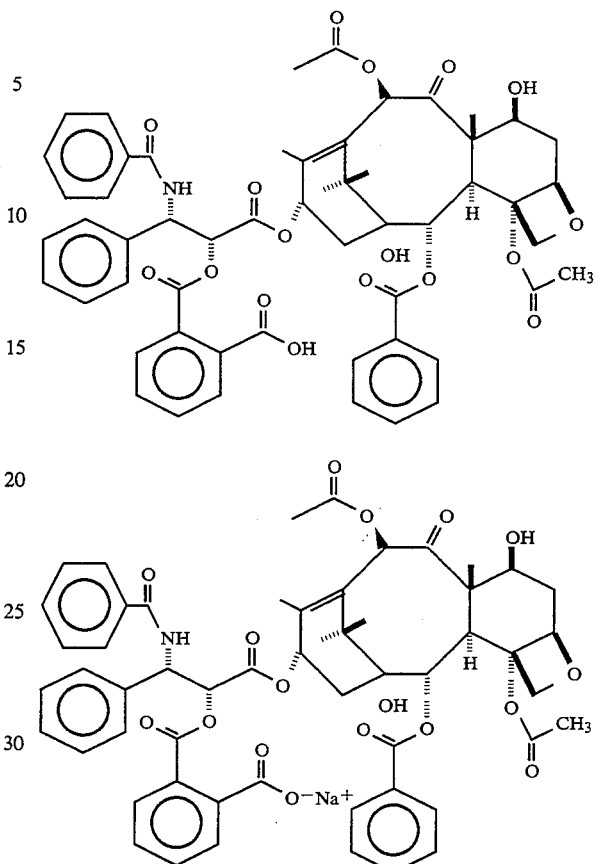

In a preferred embodiment of the present invention 2'-0-(1,4-substituted benzoyl) taxol derivatives can be obtained. These derivatives can not be prepared by the route that was used to synthesize taxol 2'-(hydrogen-1,2-benzene dicarboxylate). It has been surprisingly discovered that taxol 2'-0-benzoyl derivatives having multiple carboxylate functionalities on the phenyl ring can be synthesized via the use of protected carboxylic acid derivatives of benzene; these can not be prepared from anhydrides. It has been found that by coupling taxol with carboxylic acid derivatives of benzene, in which some, but not all, of the carboxylate groups are protected with a protecting group, followed by removal of the protecting group(s) results in the high yield synthesis of 2'-0-benzoyl taxol derivatives with carboxylate groups on the phenyl ring. In a preferred embodiment, protection of the carboxylate groups is accomplished by esterification, preferably with benzyl alcohol.

Figure 2:
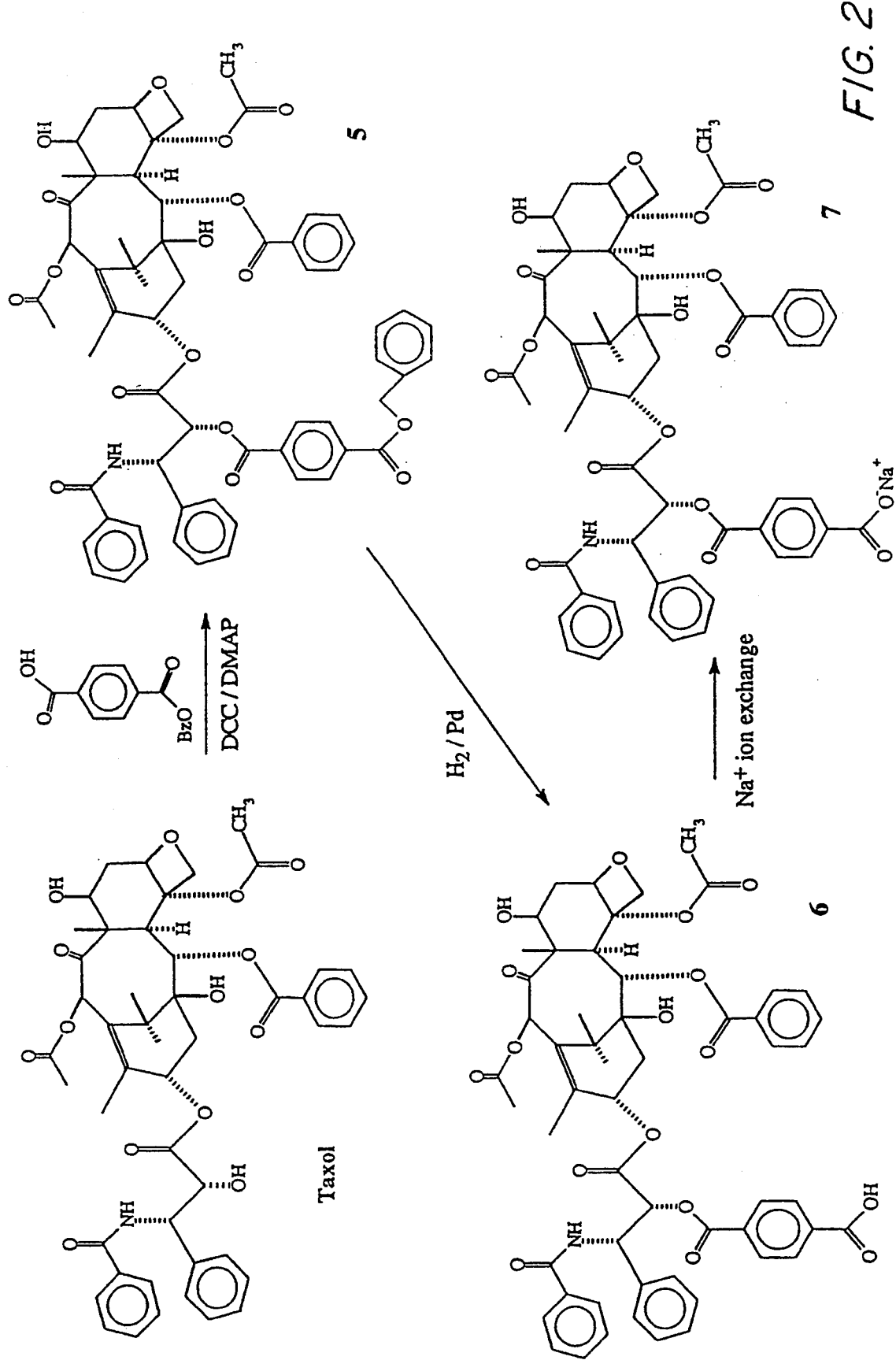
FIG. 2 illustrates the synthesis of taxol 2'-(sodium-1,4-benzenedicarboxylate) from taxol via reaction with 4-benzyloxycarbonyl benzoic acid, removal of the protecting benzyloyl group by hydrogenation over catalyst (e.g., palladium), and sodium ion exchange.

With reference to FIG. 2, the monobenzyl ester of 1,4-benzene dicarboxylic acid is coupled with taxol in the presence of dicyclohexylcarbodiimide (DCC) and 4-dimethylaminopyridine (DMAP) to yield the monobenzyl ester of taxol 2'-(1,4-benzenedicarboxylic acid) (5). This ester is converted to taxol 2'-(sodium 1,4-benzene dicarboxylate) (7) by the sequence of deprotection of the 4-benzoyl carboxy group (via hydrogenolysis) followed by ion-exchange treatment of the resulting acid (6).

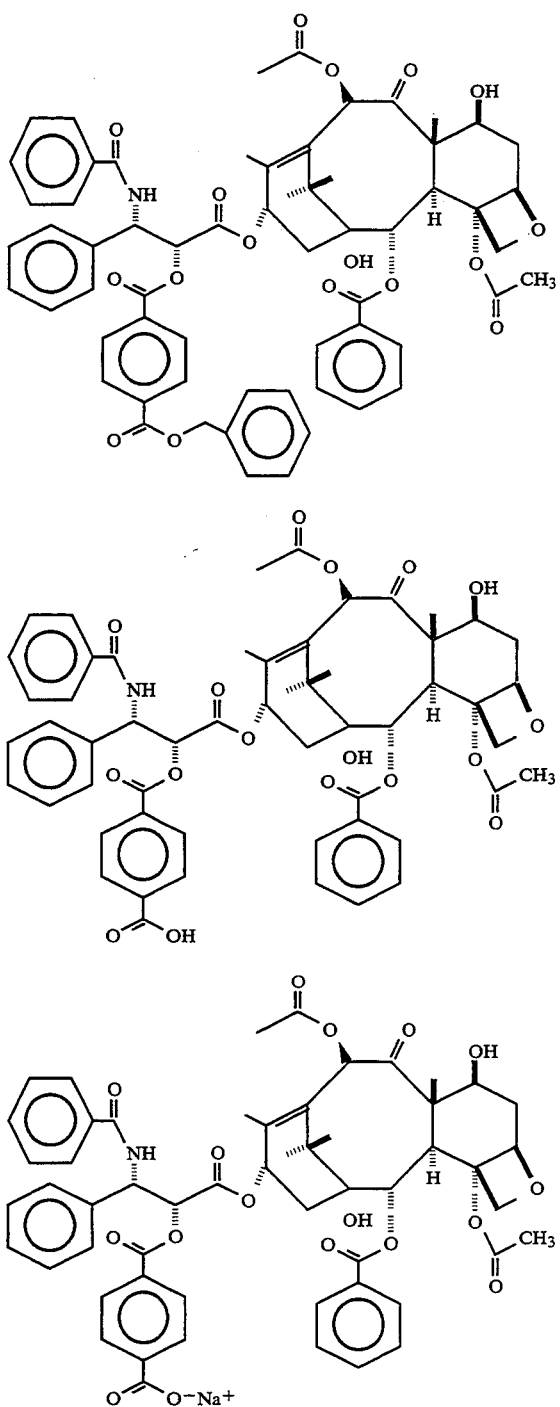

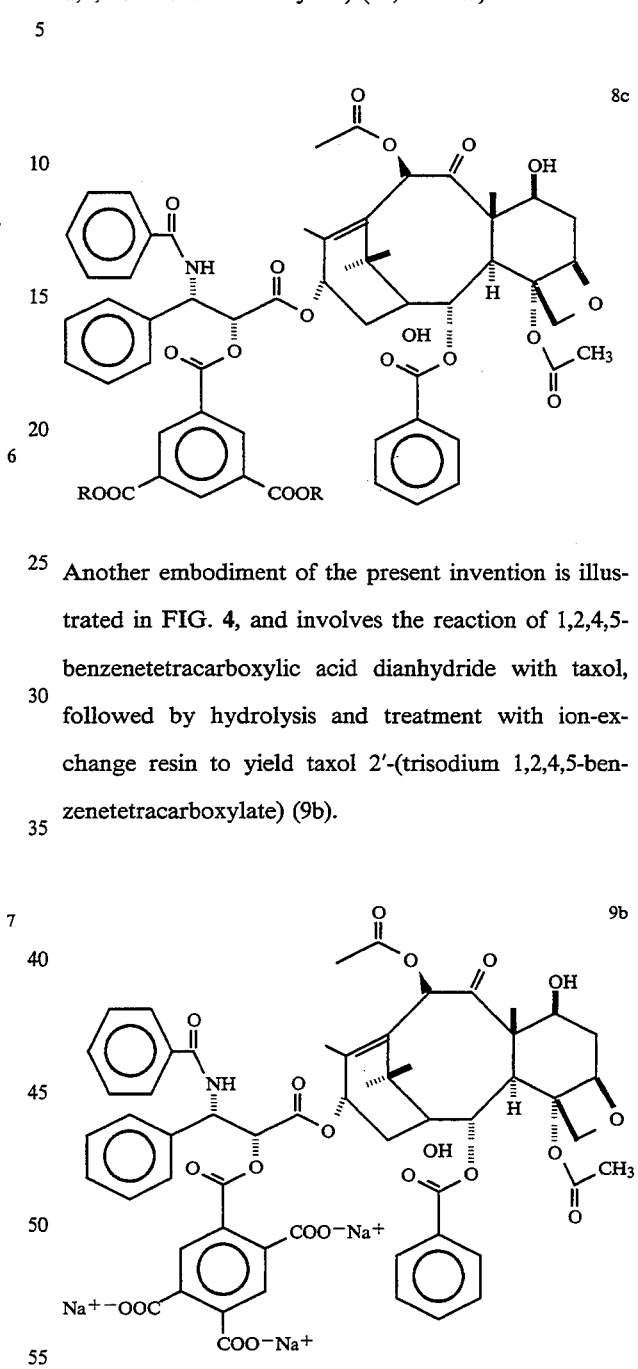

genolysis and ion-exchange to the taxol 2'-(disodium 1,3,5-benzenetricarboxylate) (80, R=Na)

Figure 4:
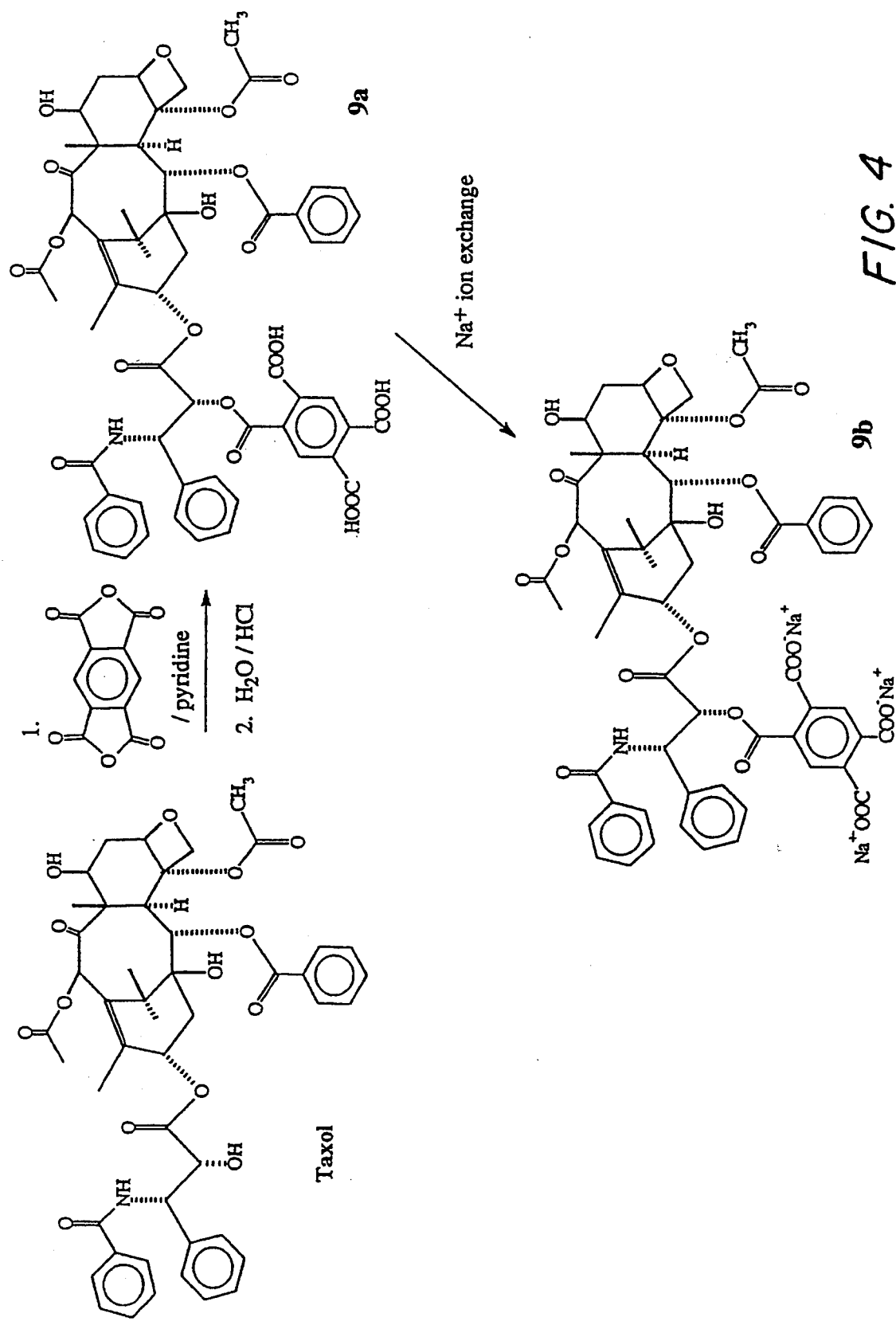
FIG. 4 illustrates the synthesis of taxol 2'-(trisodium 1,2,4,5-benzenetetracarboxylate) from taxol via reaction with 1,2,4,5-benzenetetracarboxylic dianhydride in the presence of pyridine, followed by sodium ion exchange.

Another embodiment of the present invention is illustrated in FIG. 4, and involves the reaction of 1,2,4,5-benzenetetracarboxylic acid dianhydride with taxol, followed by hydrolysis and treatment with ion-exchange resin to yield taxol 2'-(trisodium 1,2,4,5-benzenetetracarboxylate) (9b).

In a preferred embodiment, synthesis of the compounds of the present invention is achieved by first protecting the carboxylate groups on the phenyl ring of the polycarboxylic acid, which do not couple to taxol, by esterification.

Figure 3:
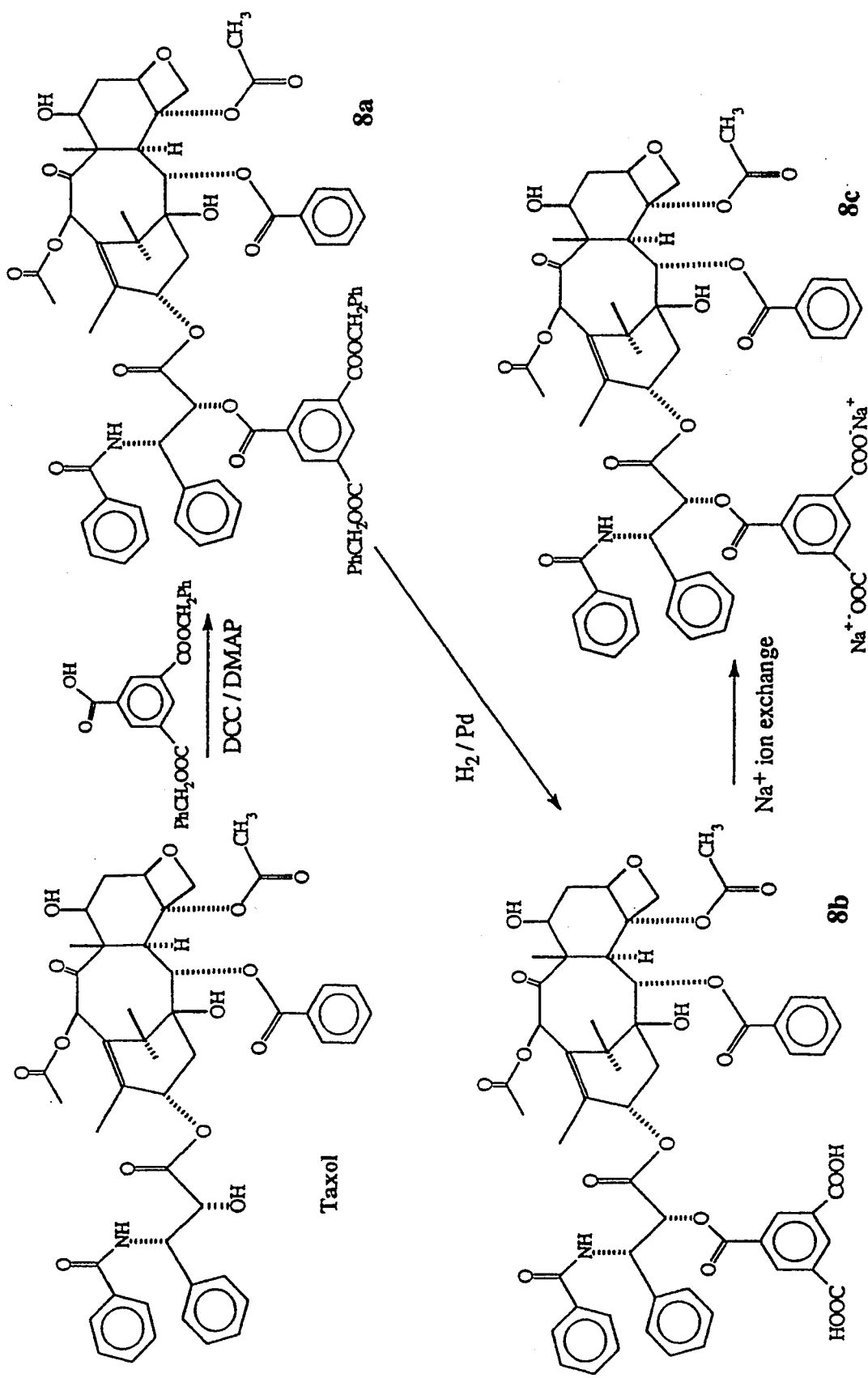
FIG. 3 illustrates the synthesis of taxol 2'-(disodium 1,3,5-benzenetricarboxylate) from taxol via reaction with 3,5-dibenzyloxycarbonyl benzoic acid in the presence of dicyclohexylcarbodiimide and 4-dimethylaminopyridine, followed by removal of the protecting groups and sodium exchange.
Figure 5:
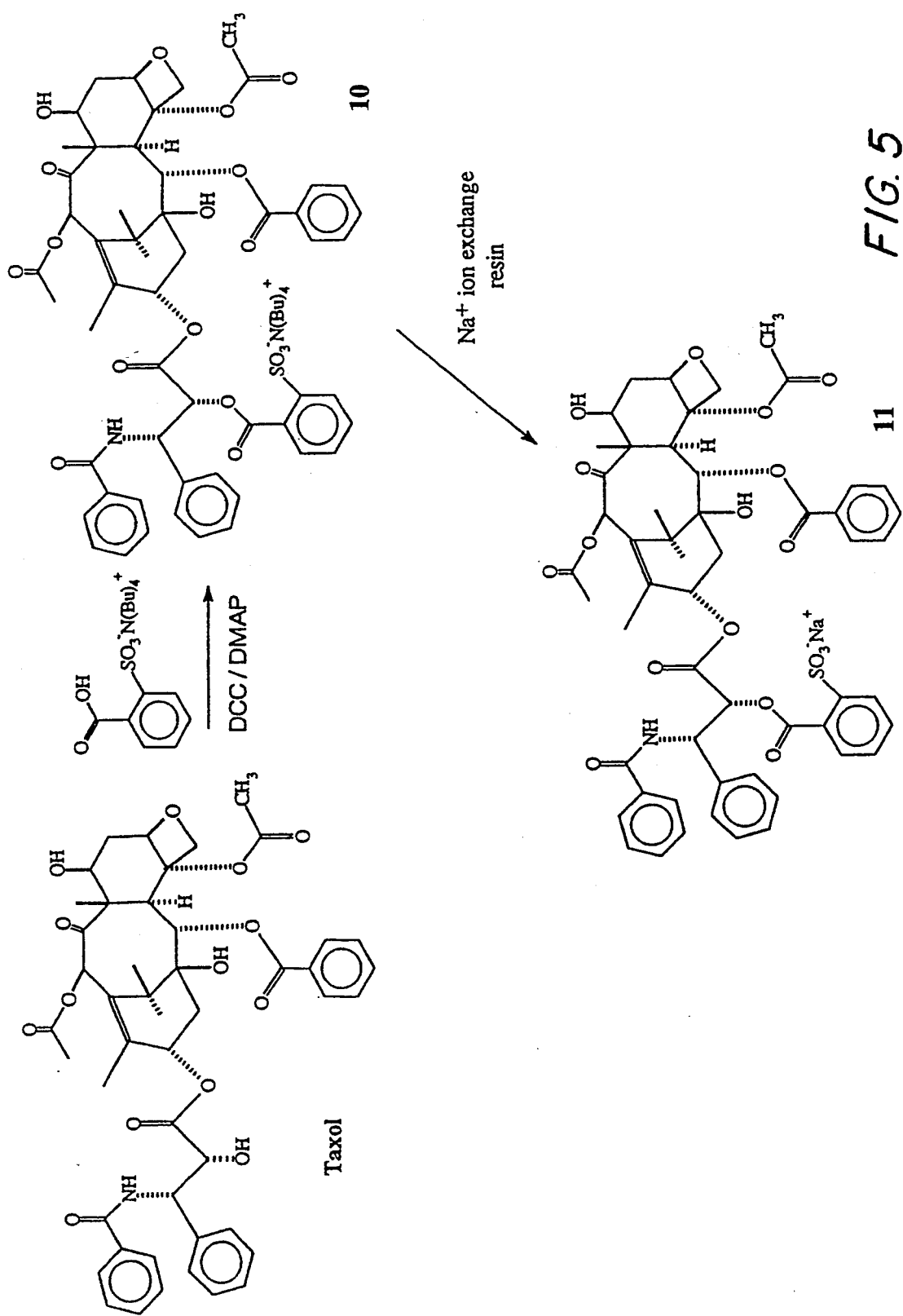
FIG. 5 illustrates the synthesis of 2'-0-(2-sulfobenzoyl) taxol sodium salt from taxol via reaction with the tetrabutylammonium salt of 2-sulfobenzoic acid in the presence of DCC and DMAP followed by sodium ion exchange.

In another aspect of the present invention, multiple substituted 2'-0-benzoyl taxol derivatives can be prepared. With reference to FIG. 3, it is preferred that the dibenzyl ester of 1,3,5-benzenetricarboxylic acid be reacted with taxol in the presence of dicyclohexylcarbodiimide, DCC, and dimethylaminopyridine, DMAP. Preferably, the resulting ester is converted-by hydro- In another aspect of the present invention, sulfonated 2'-benzoyl taxol derivatives can be prepared. In a preferred embodiment, shown in FIG. 5, treatment of the tetrabutylammonium salt of 2-sulfobenzoic acid with taxol in the presence of DCC and DMAP yielded the tetrabutylammonium salt of taxol 2'-(2-sulfobenzoate) (10), which was converted

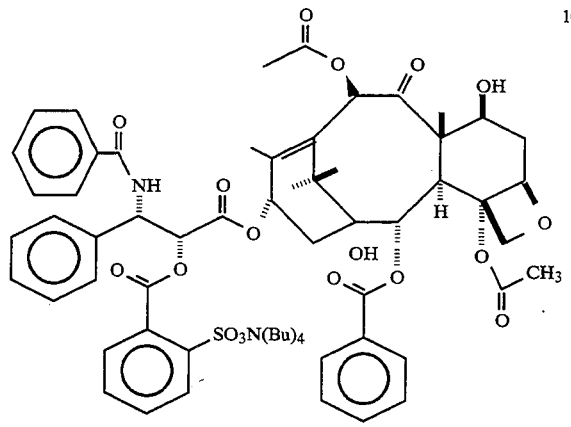

to the corresponding sodium salt (11) by ion exchange.

A similar treatment of taxol with the tetrabutylammonium salt of 4-sulfobenzoic acid yielded the sulfonate derivative (12), where X is a cation, such as sodium.

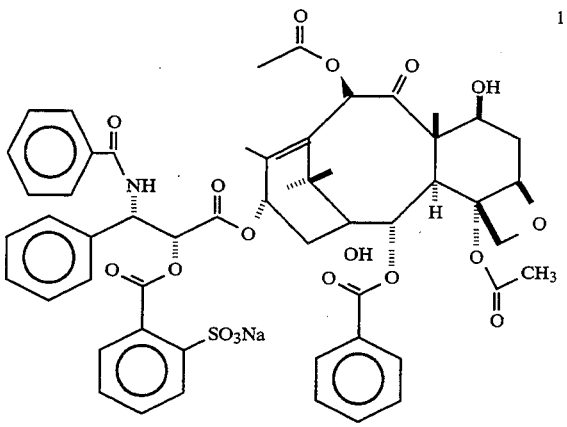

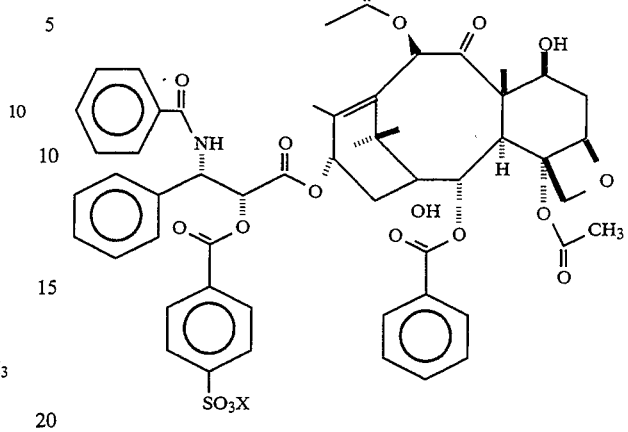

Figure 6:
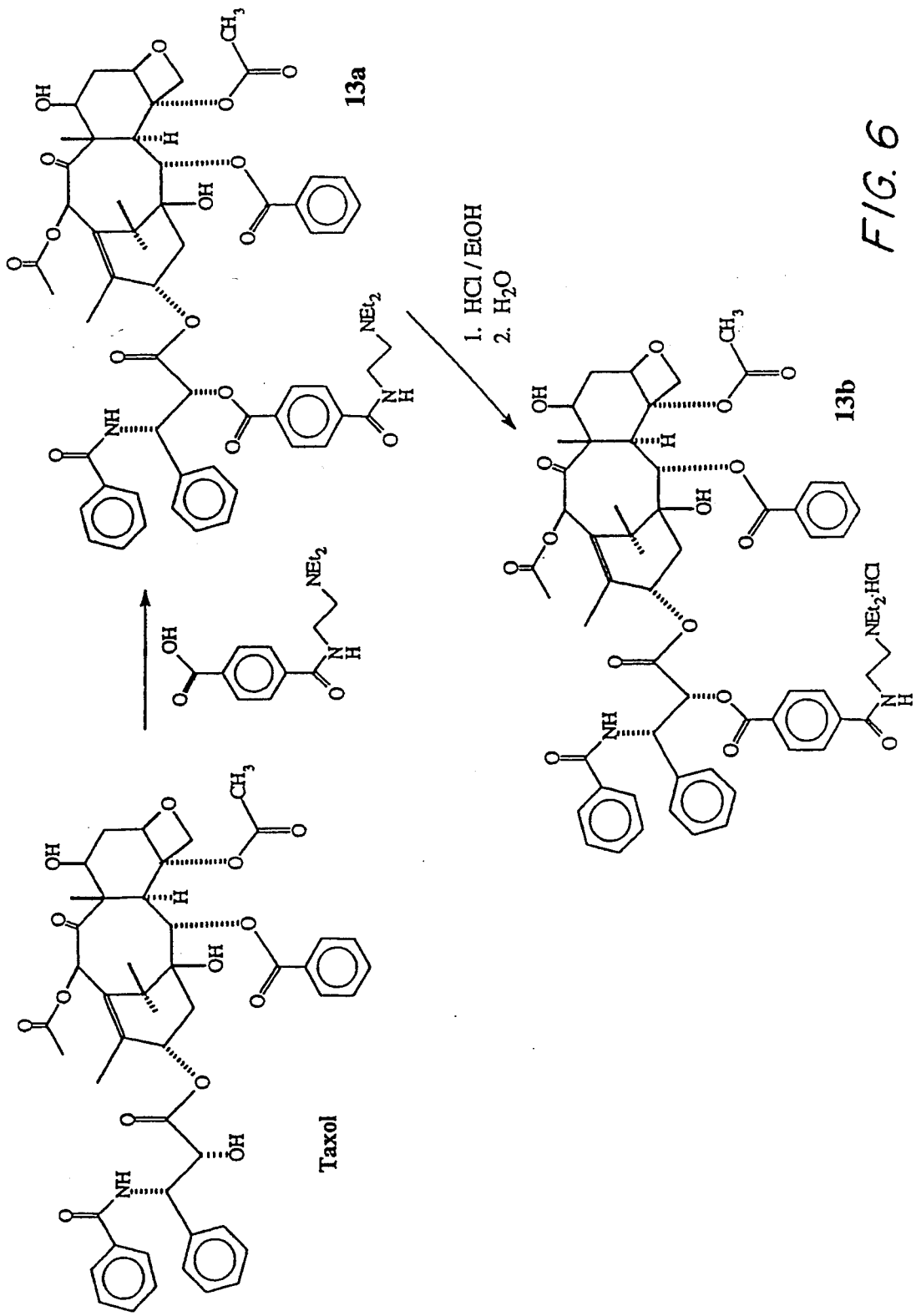
FIG. 6 illustrates the synthesis of 2'-0-[4-[2-(N,N-diethylamino)ethyl]amido]benzoyl]taxol from taxol via reaction with 4-(2-(N,N-diethylamino)ethyl)amido benzoic acid with taxol followed by treatment with hydrochloric acid.

In another embodiment of the present invention amido 2'-O-benzoyl taxol derivatives are prepared. The amido derivatives may further contain ammonio moieties. In a preferred embodiment, see FIG. 6, the amido-substituted benzene carboxylic acid (13a) was prepared by coupling taxol with 4-(2-[N,N-diethylamino)ethyl-]aminocarbonyl) benzoic acid using N,N-carbonyl-diimidazole (CDI) to yield taxol 2'-4-(2-(N,N-diethylaminoethyl)amido) benzoate.

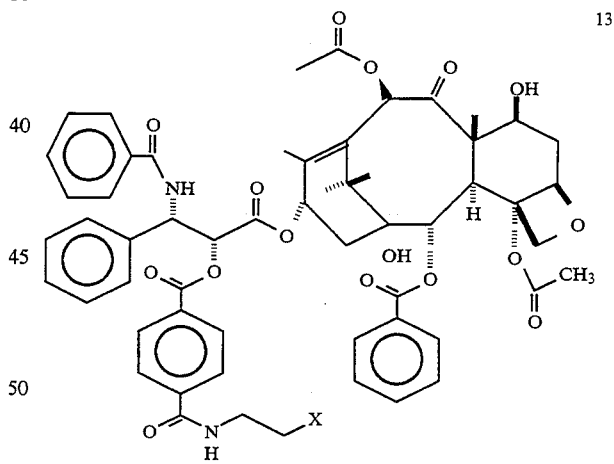

13a X = NEt$_2$
13b X = NEt$_2$.HCl

Figure 7:
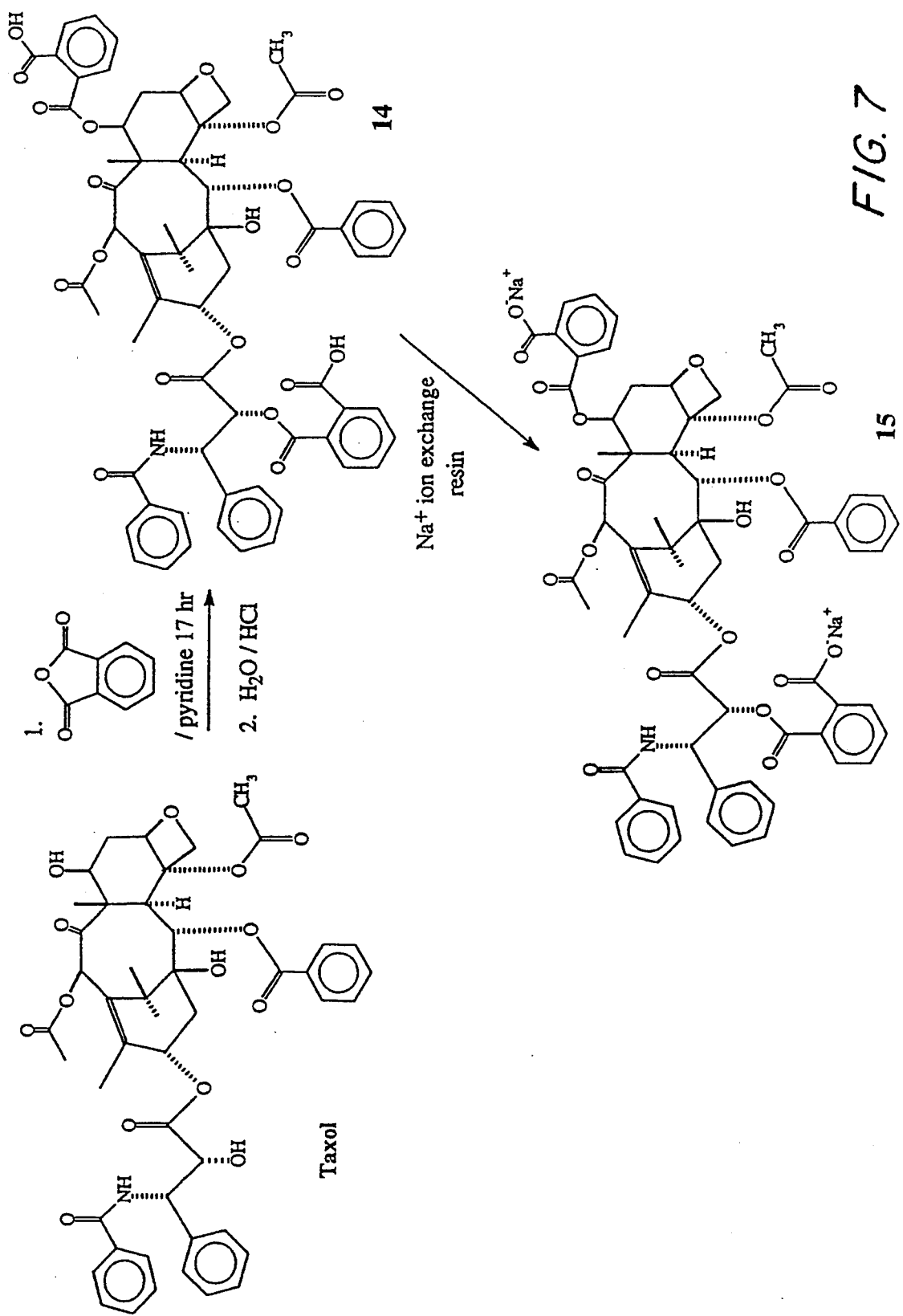
FIG. 7 illustrates the synthesis of taxol 2',7-di(sodium 1,2-benzenedicarboxylate) from taxol via reaction with phthalic anhydride in the presence of pyridine for an extended time followed by sodium ion exchange.

Treatment of 13a with HCl yielded the hydrochloride salt 13b. In yet another aspect of the present invention 2',7-dibenzoyl substituted derivatives of taxol are formed. In a preferred embodiment, the derivatives (15) and (19) were prepared by reaction of taxol under more vigorous conditions with phthalic anhydride, see FIG. 7, or with the monobenzyl ester of 1,4-benzenedicarboxylic acid.

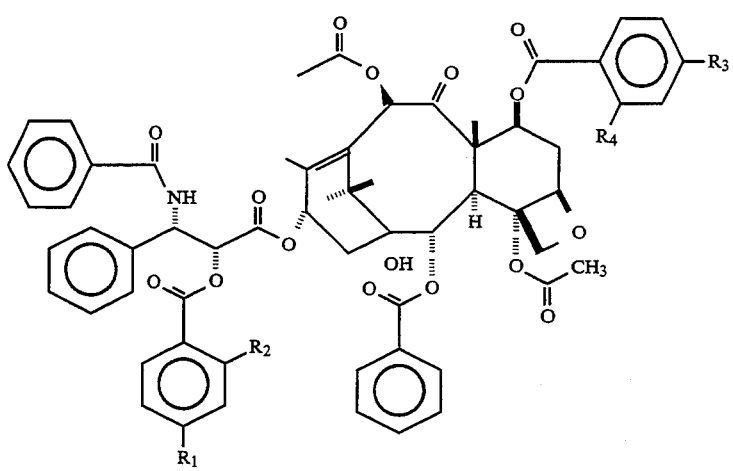

14

14 $R_1 = R_3 = H; R_2 = R_4 = COOH$
15 $R_1 = R_3 = H; R_2 = R_4 = COONa$
16 $R_1 = R_3 = COOCH_2Ph; R_2 = R_4 = H$
17 $R_1 = COOCH_2Ph, R_3 = COOH; R_2 = R_4 = H$
18 $R_1 = R_3 = COOH; R_2 = R_4 = H$
19 $R_1 = R_3 = COONa; R_2 = R_4 = H$

EXAMPLES

The following nonlimiting examples provide specific synthesis methods for preparing prodrugs of taxol and taxol congeners of the present invention. All technical and scientific terms used herein have the same meaning as commonly understood by one of ordinary skill in the art. Other methods and materials similar or equivalent to those described herein can be used in the practice or testing of the present invention.

Taxol 2'-(sodium-1,2-benzenedicarboxylate) (4)

a. Taxol 2'-(Hydrogen 1,2-benzenedicarboxylate) (3). Taxol (50.0 mg, 0.059 mmol) was added to a solution of phthalic anhydride (Aldrich, 124.3 mg, 0.84 mmol) in dry pyridine (6 ml) with stirring at room temperature; the mixture was then stirred at room temperature for 0.5 hours. The solution was evaporated to dryness (<35° C. in vacuo), and the residue submitted to partition between ethyl acetate and $H_2O$. The ethyl acetate layer was washed with 0.36% HCl, then $H_2O$, and evaporated to dryness (in vacuo, <35° C.) to yield a crude product. The crude product was dissolved in 2 ml of $CH_2Cl_2$:acetone, 5:1 and added to a Sephadex LH-20 column (8g). The column was eluted with hexanes/$CH_2Cl_2$ and $CH_2Cl_2$/acetone mixtures; evaporation of the fractions eluted with $CH_2Cl_2$/acetone, 5:1, yielded 3 (55.8 mg, 95%): mp 156°–157° C. (recrystallized from $CH_2Cl_2$). The principal peaks in FAB-MS were: m/z 1024 [M+Na]+, 1002 [M+1]+, the $^1$H-NMR spectrum (CD]OD, 270 MHz) showed the following peaks: 1.45(6H, s, 16-$CH_3$+17-$CH_3$), 1.62 (3H, s, 19-$CH_3$), 2.00 (3H, s, 18-$CH_3$), 2.16 (3H, s, 10-OAc), 2.40 (3H, s, 4-OAc), 3.83 (1H, d, 7.0, 3-H), 4.18 (2H, br.s, 20-H), 4.34 (1H, dd, 10.1, 6.3 7-H), 4.99 (1H, d, 8.0, 5-H), 5.64 (1H, d, 7.0, 2-H), 5.72 (1H, d, 6.6, 2'-H), 5.95 (1H, d, 6.6, 3'-H), 6.16 (1H, br.t, 9.2, 13-H), 6.46 (1H, s, 10-H), 7.28–7.85 (18H, m, NBz,+OBz(meta, para)+3'Ph+NH+ARH*4), 8.12 (2H, d, 8.0, OBz(ortho)).

b. Taxol 2'-(sodium 1,2-benzenedicarboxylate) (4). To a solution of 3 (40.0 mg, 0.040 mmol) in acetone (0.5 ml) was added $NaHCO_3$ (3.6 mg, 0.040 mmol) in 0.2 ml $H_2O$. The solution was evaporated to dryness (<30° C., in vacuo) to a gummy solid, $H_2O$ added, and the solution sonicated and freeze-dried to yield 4 (37.5 mg, 94%): mp 190°–191° C. (MeOH). FAB-MS: m/z 1024 [M+1]+; $^1$H-NMR (($CD_3)_2CO$, 270 MHz): 1.17 (6H, s, 16-$CH_3$+17-$CH_3$), 1.65 (3H, s, 19-$CH_3$), 2.04 (3H, s, 18-$CH_3$), 2.14 (3H, s, 10-OAc), 2.40 (3H, s, 4-OAc), 3.81 (1H, d, 7.0, 3-H), 4.15 (2H, br.s, 20H), 4.41 (1H, m, 7H), 4.95 (1H, br.d, 9.5, 5-H), 5.67 (1H, d, 7.0, 2-H), 5.75 (1H, d, 7.1, 2'-H), 5.93 (1H, dd, 7.1, 2.8, 3'-H), 6.15 (1H, t, 8.8, 13-H), 6.42 (s, 10-H), 7.20–8.20 (20H, m, NBz+OBz+3'-Ph+NH+Ar-H*4).

Taxol 2'-(sodium 1,4-benzenedicarboxylate) (7)

a. 4-Benzyloxycarbonylbensoic acid was prepared by classical procedures from terephthaloyl chloride. Both carboxyl groups were first protected as benzyl esters (EI-MS: m/z 346 [M+]), then one ester was deprotected by partial hydrolysis using LiOH to form the monoester (EI-MS: m/z 256[M+]).

b. 2'-(Benzyloxycarbonylbenzoyl)-taxol (5). To a solution of 4-benzyloxycarbonyl benzoic acid (16.5 mg, 0.065 mmol) in dry $CH_2Cl_2$(5 ml) was added DCC (120.7 mg, 0.59 mmol) and 4-DMAP (14.0 mg, 0.12 mmol). The solution was stirred at room temperature for 0.5 h, then taxol (50.0 mg, 0.059 mmol) was added and stirring continued at room temperature for several hours (checked by TLC). When the reaction was completed, 3 ml of $CH_2Cl_2$ were added, the solution was filtered through Celite and evaporated to dryness (<30° C. in vacuo). The product was purified by PTLC($SiO_2$, $CH_2Cl_2$:MeOH, 100:15) to yield 5 (43.0 mg, 67%): $^1$H-NMR ($CDCl_3$, 270 MHz): 1.13 (3H, s, 16-$CH_3$), 1.23 (3H,s, 17-$CH_3$), 1.67 (3H,s, 19-$CH_3$), 1.96 (3H,s, 18-$CH_3$), 2.23 (3H,s, 10-OAc), 2.44 (3H,s, 5-OAc), 3.81 (1H, d, 7.1, 3-H), 4.18 (1H, d, 8.3,, 20-H), 4.31 (1H, d, 8.3, 20'-H), 4.44 (1H, dd, 11.1, 6.7, 7-H), 4.97 (1H, br.d, 7.5, 5-H), 5.39 (2H, s, —OC$CH_2$Ph), 5.67 (1H, d, 7.1, 2-H), 5.69 (1H, d, 3.8, 2'-H), 6.05 (1H, dd, 9.0,3.8,3'-H), 6.26 (1H, br.t, 8.8, 13-H), 6.29 (1H, s, 10-H), 6.97 (1H, d, 9.0 NH), 7.30–7.70 (16H, m, NBz (meta,para) +OBz (meta, para) +3'Ph+Bn), 7.75 (2H, d, 8.2, NBz (ortho)), 8.03 (2H,d, 8.4, AR-H*2), 8.12 (2H, d, 8.4, Ar-H*2); 8.15 (2H, d, 8.5, OBz (ortho)).

c. Taxol 2'-(hydrogen 1,4 benzene dicarboxylate) (6) To a solution of 5 (26.1 mg, 0.024 mmol) in AcOEt (1 ml) and AcOH (1 drop) was added Pd/C (10%, 2.4 mg) and the mixture stirred at room temperature under $H_2$ for 6.5 h. The Pd/C was filtered off and the solution evaporated to dryness (<30° C., in vacuo) to yield 6 (22.1 mg, 92%): top: 185°–186° C. (AcOEt); FAB-MS: m/z 1024 [M+Na]+, 1002 [M+1]+; $^1$H-NMR (CDCl$_3$, 270 MHz): 1.15 (3H, s, 16-CH$_3$, 1.26 (3H, s, 17-CH$_3$), 1.69 (3H, s, 19-CH$_3$), 2.00 (3H, s, 18-CH$_3$), 2.24 (3H, s, 10-OAc), 2.49 (3H, s, 4-OAc); 3.84 (1H, d, 7.0, 3-H), 4.21 (1H, d, 8.6, 20-H), 4.33 (1H, d, 8.6, 20'-H), 4.46 (1H, dd, 11.2, 6.8, 7-H), 4.99 (1H, br.d, 7.6, 5-H), 5.67 (1H, d, 3.6, 2'-H), 5.70 (1H, d, 7.0, 2-H), 6.12 (1H, dd, 9.2, 3.7, 3'-HH), 6.31 (1H, t, 9.2, 13-H), 6.31 (1H, s, 10-H), 7.20–7.70 (12H, m NBz (meta, para)+OBz (meta, para)+3'Ph+NH)), 7.78 (2H, d, 7.2, NBz (ortho)), 7.95 (2H, d, 8.4 Ar-H*2), 2H, d, 8.4, ArH2), 8.13 (2H, d, 7.2, OBz (ortho)).

d. Taxol 2'-(sodium 1,4-benzenedioarboxylate) (7) A solution of 6 (48.2 mg, 0.048 mmol) in acetone (0.5 ml), was treated with 0.2 ml of a solution of NaHCO$_3$ (4.05 mg, 0.048 mmol) in H$_2$O with stirring at room temperature. The solution was evaporated to a gummy solid (<30° C. in vacuo), 1 ml of HO was added, the solution was sonicated and freeze-dried to yield 7 (47.3 mg, 96%). top: 221°–222° C. (MeOH); FAB-MS: m/z 1024 [M]+; $^1$H-NMR ((CD$_3$)$_2$CO, 270 MHz: 1.19 (6H, br.s, 16-CH$_3$+17-CH$_3$), 1.66 (3H, s, 19-CH$_3$), 2.04 (3H, s, 18-CH$_3$), 2.15 (3H, s, 10-OAc), 2.48 (3H, s, 4-OAc), 3.87 (1H, d, 6.8, 3-H), 4.16 (2H, br.s, 20-H), 4.43 (1H, m, 7-H), 4.97 (1H, br.d, 9.0, 5-H), 5.68 (1H,d, 6.8 2-H), 5.73 (1H, d, 6.5, 2'-H), 6.14 (2H, m, 3'-H+13-H), 6.43 (1H, s, H-10, 7.2–8.2 (20H, m, NBz+NH +Ar-H-4+3'-Ph).

Taxol 2'-(disodium 1,3,5-bensenetricarboxylate (8c).

a. 3,5-Benzyloxycarbonylbenzoic acid was prepared by similar procedures to those described above from 1,3,5-benzenetricarbonyl chloride. The carboxyl groups were first protected as benzyl esters (EI-MS: m/z 480 [M+]) and selective hydrolysis using LiOH yielded the monoacid (EI-MS: m/z 390 [M+]).

b. 2'-(3,5-Dibenzyloxycarbonylbenzoyl)taxol (8a). To a solution of 3,5-Benzyloxycarbonylbenzoic acid (91.0 mg, 0.234 mmol) in dry CH$_2$Cl$_2$ (0.6 ml) and dry THF (0.3 ml) was added DCC (241.0 mg, 1.17 mmol) and 4-DMAP (28.5 mg, 0.234 mmol) and the mixture stirred at room temperature for 0.5 h. Taxol (100.0 mg, 0.117 mmol) was then added, and stirring at room temperature for 45 h followed by work-up as described for compound 5 gave 14 (121.8 mg, 85%). top: 154°–155° C. (acetone). FAB-MS: m/z 1226 [M+1]+; $^1$H-NMR (CDCl$_3$, 270 MHz): 1.06 (3H, s, 16-CH$_3$), 1.13 (3H, s, 17-CH$_3$), 1.69 (3H, s, 19-CH$_3$), 1.98 (3H, s, 18-CH$_3$), 2.21 (3H, s, 10-OAc), 2.49 (3H, s, 4-OAc), 3.82 (1H, d, 7.1, 3-H), 4.12 (1H, d, 8.5, 20-H), 4.19 (1H, d, 8.5, 20'-H), 4.46 (1H, m, 7-H), 4.97 (1H, br.d, 9.9, 5-H), 5.40 (4H, s, OcCH$_2$Ph*2), 5.65 (1H, d, 3.3, 2-'H), 5.68 (1H, d, 7.1, 2-H), 6.07 (1h, dd, 9.0, 3.3, 3'-H), 6.27 (1H, t, 9.0, 13-H), 6.30 (1H, s, 10-H), 6.98 (1H, 9.0, NH), 7.26–7.54 (21H, m, NBz(meta, para)+OBz(Meta, para)+3'Ph+Bm*2), 7.73 (2H, d, 71 NBz(ortho)), 8.14 (2H, d, 7.0 (Bz(ortho)), 8.82 (2H (2H, d, 1.6, Ar-H*2), 8.94 (1H, d, 1.6, t, Ar-H).

c. Taxol 2'-(dihydrogen 1,3,5-bensenetricarboxylate) (8b). To a solution of 8a (120.0 mg, 0.098 mmol) in AcOEt (8 ml) and AcOH (15 drops) was added Pd/C (10%, 19.6 mg), and the mixture hydrogenated for 5 h. The solution was filtered, the filtrate evaporated to dryness (<35°, in vacuo) and the residue partitioned between AcOEt and H$_2$O. The AcOEt layer was evaporated to dryness (<35°, in vacuo) to yield 8b (102.0 mg, 99.5%) . Mp 209°–210° C. (AcOEt); FAB-MS: m/z 1136 [M+thioglycerol-H$_2$O)]+, 1046 [M+1]+; $^1$H-NMR (CD$_3$OD, 270 MHz): 1.13 (6H, s, 16CH$_3$+17CH$_3$), 1.66 (3H, s, 19-CH$_3$), 1.99 (3H, s, 18-CH$_3$), 2.15 (3H, s, 10-OAc), 2.43 (3H, s, 4-OAc), 3.83 (1H, d, 7.1, 3-H), 4.10 (2H, s, 20-H), 4.19 (1H, m, 7-H), 5.00 (1H, br.d, 9.0, 5-H), 5.63 (1H, d, 7.1, 2-H), 5.68 (1H, d, 6.9, 2'-H), 6.00–6.20 (2H, m, 3'-H+13-H), 6.47 (1H, s, 10-H), 7.30–7.68 (12H, m, NBz (meta, para)+OBz(meta, para)+3'Ph+NH), 7.84 (2H, d, 6.8, NBz(ortho)), 8.10 (2H, d, 7.1, OBz(ortho)), 8.88 (3H, d, 2, 5, ArH$^3$).

d. Taxol 2'-(disodium 1,3,5-benzenetricarboxylate) (8c). Compound 8b (102.0 mg, 0.098 mmol) was dissolved in 4.0 ml of acetone, and treated with a solution of NaHCO$_3$ (16.5 mg, 0.196 mmol) in H$_2$O (0.5 ml). The solution was azeotroped to dryness with MeCN to yield the sodium salt 8c (105.2 mg, 98,6%). Mp 265°–266° C. (MeOH). FAB-MS: m/z 1181 (M+Na*4]+, 1157 [M+Na*3-1]+, 1090 [M+1]+; $^1$H-NMR (CD$_3$OD, 270 MHz): 1.17 (6H, s, 16-CH$_3$+17-CH$_3$ ), 1.67 (3H, s, 19-CH$_3$), 2.03 (3H, s, 18-CH$_3$), 2.15 (3H, s, 10-OAc), 2.43 (3H, s, 4-OAc), 3.89 (1H, d, 7.2, 3-H), 4.20 (2H, s, 20-H), 4.40 (1H, m, 7-H), 4.97 (d, 7.5, 5-H), 5.67 (1H, d, 7.2, 2-H), 5.72 (1H, d, 3.7, 2'-H), 6.13–6.25 (2H, m, 13H+3'-H), 6.47 (1H, s, 10-H), 7.30–7.86 (12H, m, NBz (meta, para)+3'Ph+NH), 7.88 (2H, d, 6.7, NBz(ortho)), 8.13 (2H, d, 7.2, OBz(ortho)), 8.79 (2H, s, Ar-H*2), 8.88 (1H, s, Ar-H).

Taxol 2'-(trisodium 1,2,4,5-benzenetetracarboxylate) (9b)

a. Taxol2,-trihydrogen 1,2,4,5-benzenedicarboxylate) (9a). To a solution of sublimed 1,2,4,5-benzenetetracarboxylic dianhydride (28.1 mg, 0.128 mmol) in dry THF (1 ml), was added dry pyridine (0.038 ml, 0.47 mmol), and taxol (100.0 mg, 0.117 mmol) while stirring; stirring was continued at r.t for 1 h. The product was worked up by partition between EtOAc (20ml) and H$_2$O (10 ml). The EtOAc layer was washed with 0.36% HCl (10 ml), then H$_2$O (10 ml), and extracted with 5% NaHCO$_3$ solution. The NaHCO$_3$ layer was acidified with 3.6% HCl to pH 4, and extracted with EtOAc (20 ml×2). The AcOEt layers were washed with H$_2$O (10 ml), then evaporated to dryness (<35° C., in vacuo) to yield 9a (117.5 mg, 92%). Mp 189°–190° C. (AcOEt). FAB-MS: m/z 1092 [M+3]+, 1190 [M+1]+; $^1$H-NMR (CD$_3$OD, 270 MHz): 1.10 (6H, s, 16-CH$_3$+17-CH$_3$), 1.62 (3H, s, 19-CH$_3$), 1.91 (3H, s, 18-CH$_3$), 2.12 (2H, s, 10-OAc), 2.38 (3H, s, 4-OAc), 3.82 (1H, d, 7.2, 3-H), 4.18 (2H, s, 20-H), 4.36 (1H, m, 7-H), 4.98 (1H, d, 8.7, 5H), 5.47 (1H, d, 7.2, 2-H), 5.75 (1H, d, 6.0, 2'-H), 6.00 (1H, d, 6.0, 3'-H), 6.18 (1H, t, 9.1, 13-H), 6.45 (1H, s, 10-H), 7.29–8.14 (18H, m, Ar-H×17+NH).

b. Taxol 2,-(trisodium 1,2,4,5-benzenetetracarboxylic acid) (9b). Compound 9a (109.0 mg, 0.1 mmol) was dissolved in acetone (2 ml) and treated with a solution of NaHCO$_3$ (25.2 mg, 0.3 mmol), in H$_2$O. The mixture was stirred at room temperature for 0.5 h, then evaporated to dryness as an azeotrope with MeCN, (<35° C., in vacuo) to yield 9b (115.0 mg, 99.6%). Mp 275-276° C. (H20). FAB-MS: m/z 1156 [M+1]+, 1133 [M-Na+1]+, 1112 [M-2Na+1]+; $^1$H-NMR (CD$_3$OD, 270 MHz): 112 (6H, s, 16-CH$_3$+17-CH$_3$), 1.66 (3H, s, 19-

CH$_3$), 1.97 (3H, s, 18-CH$_3$), 2.15 (3H, s, 10-OAc), 2.39 (3H, s, 4-OAc), 3.84 (1H, d, 7.0, 3-H), 4.19 (2H, s, 20-H), 4.37 (1H, dd, 9.3, 6.8, 7-H), 5.00 (1H, br.d, 8.1, 5-H), 5.65 (1H, d, 7.0, 2-H), 5.78 (1H, d, 6.5, 2'-H), 5.99 (1H, d, 6.5, 3'-H), 6.16 (1H, br.t, 9.1, 13-H), 6.47 (1H, s, 10-H), 7.30–8.15 (18H, m, Ar-H*17+NH).

2'-(2-Sulfobenzoyl)taxol, sodium salt (11)

a. 2-Sulfobensoic acid bis-tetrabutylammonium salt (20) was prepared from 2-sulfobenzoic acid cyclic anhydride by treatment with excess tetrabutylammonium hydroxide. FAB-MS: m/z 927 [M+NBu$_4$*2]$^+$, 685 [M+NBu$_4$]$^+$, 684 [M+NBu$_4$-1]$^+$, 242 [N(Bu)$_4$]$^+$.

b. 2'-(2-Sulfobenzoyl)taxol, tetrabutylammonium salt (10). To a solution of 2-sulfobenzoic acid, tetrabutylammonium salt, (97.5 mg, 0.22 mmol) in dry CH$_2$Cl$_2$ (4.0mg), was added DCC (412.0) mg, 2.0 mmol) and 4-DMAP (49.0 mg, 0.4 mmol) with stirring at room temperature for 0.5 h followed by taxol (171.0 mg, 0.2 mmol), and continued stirring for 24 h. Work-up as described for 5, with purification by PTLC (SiO$_2$, F254, CH$_2$Cl$_2$:MeOH=100:15), gave 10 (250.0 mg, 97.8%. Mp 185°–186° C. (acetone). FAB-MS: m/z 1520 [M+NBu$_4$]$^+$; $^1$H-NMR (CDCl$_3$, 270 MHz): 0.91 (12 H, t, 7.2 NCH$_2$CH$_2$CH$_2$CH$_3$×4), 1.11 (3H, s, 16-CH$_3$), 1.20 (3H, s, 17-CH$_3$), 1.23 (8H, dd, 7.2, 7.2, NCH$_2$CH$_2$CH$_2$CH$_3$×4), 1.41 (8H, br.s, NCH$_2$CH$_2$CH$_2$CH$_3$×4), 1.65 (3H, s, 19-CH$_3$), 1.93 (3H, s, 18-CH$_3$), 2.17 (3H, s, 10-OAc), 2.22 (3H, s, 4-OAc), 3.06 (8H, dd, 9.6, 7.4, NCH$_2$CH$_2$CH$_2$CH$_3$×4), 3.72 (1H, d, 7.5, 3-H), 4.12 (1H, d, 7.9, 20-H), 4.26 (1H, d, 7.9, 20'-H), 4.43 (1H, m, 7-H), 4.90 (1H, d, 8.2, 5-H), 5.46 (1H, d, 7.5, 2-H), 5.61 (2H, d, 6.6, 3'-H+2'-H), 6.03 (1H, br.s, 13-H), 6.29 (1H, s, 10-H), 7.08–8.11 (20H, m, NBz+OBz+3'-Ph+Arx4+HN), 9.03 (1H, br.s, NH).

c. 2'-(2-Sulfobenzoyl) taxol, sodium salt (11). A mixture of 10 (205.0 mg, 0.16 mmol), Dowex-50 ion exchange resin (Na+form, 4.0 ml) and H$_2$O (4 ml), was stirred at room temperature for 0.5 h and filtered through a small column containing 4.0 ml of the same resin, and washed with H$_2$O (6×5 ml). The filtrate and washings were evaporated as an azeotrope with MeCN (3×5 ml) to dryness (in vacuo, <35° C.) to yield 11 (173.4 mg, 79%). Mp 235°–236° C. (H$_2$O). FAB/MS: m/z 1082 [M+Na]$^+$, 1060 [M+1]$^+$; $^1$H-NMR (CD$_3$OD, 270 MHz): 1.15 (3H, s, 16-CH$_3$), 1.18 (3H, s, 17-CH$_3$), 1.63 (3H, s, 19-CH$_3$), 1.84 (3H, s, 18-CH$_3$), 2.17 (3H, s, 10-OAc), 2.28 (3H, s, 4-OAc), 3.83 (1H, d, 6.6, 3-H), 4.17 (2H, s, 20-H), 4.35 (1H, dd, 9.8, 7.1, 7-H), 4.96 (1H, d, 8.4, 5-H), 5.64 (1H, d, 6.6, 2-H), 5.65 (1H, d, 6.8, 2'-H), 5.74 (1H, d, 6.8, 3'-H), 6.14 (1H, br.t, 8.2, 13-H), 6.46 (1H, s, 10-H), 7.22 (15H, m, NBz (meta,para)+OBz (metha,para)+3'-Ph+NH+Ar-Hx3), 7.88 (2H, d, 8.4, NBz(ortho)), 8.00 (1H, d, 7.0, ArH), 8.12 (2H, d, 8.5, OBz (ortho)).

2'-(4-Sulfobenzoyl)taxol, sodium salt a. 4-Sulfobenzoic acid tetrabutylammonium salt. 4-Sulfobenzoic acid was treated with tetrabutylammonium hydroxide (2 equivalents) to yield the tetrabutylammonium salt. FAB-MS: m/z 927 [M+(NBu$_4$)*2]$^+$, 685 [M+NBu$_4$]$^+$ 242 [N(Bu)$_4$]$^+$.

b. 2'-(4-Sulfobenzoyl)taxol, tetrabutylammonium salt. To a solution of 4-sulfobenzoic acid tetrabutylammonium salt (1.7.0 mg, 0.22 mmol) in dry CH$_2$Cl$_2$ (4.0 ml) were added DCC (412.0 mg, 2 mmol) and 4-DMAP (49.0 mg, 0.4 mmol), the solution stirred at room temperature for 0.5 h, then taxol (171.0 mg, 0.2 mmol) was added and the solution stirred for 64 h. Work-up as described for 5 (filtration and PTLC) yielded the tetrabutylammonium salt of 2'-(4-sulfobenzoyl)taxol (12) (190.0 mg, 89.7%). Mp 190°–191° C. (acetone). FAB-MS: m/z 1521 [M+N(Bu)$_4$+1]$^+$; $^1$H-NMR (CDCl$_3$, 270 MHz): 0.98 (12H, t, 7.2 NCH$_2$CH$_2$CH$_2$CH$_3$ ×4), 1.11 (3H, s, 16-CH$_3$), 1.21 (3H, s, 17-CH$_3$), 1.41 (8H, dd, 7.5, 7.2 NCH$_2$CH$_2$CH$_2$CH$_3$×4), 1.62 (8H, m, NCH$_2$CH$_2$CH$_2$CH$_3$×4), 1.66 (3H, s, 19-CH$_3$), 1.93 (3H, s, 18-CH$_3$ ), 2.22 (3H, s, 10-OAc), 2.50 (3H, s, 4-OAc), 3.25 (8H, t, 8.3, NCH$_2$CH$_2$CH$_2$CH$_3$×4), 3.78 (1H, d, 7.1, 3-H), 4.17 (1H, d, 8.3, 20-H), 4.29 (1H, d, 5.1, 2'-H), 4.53 (1H, m, 7-H), 4.96 (1H, d, 8.8, 5-H), 5.65 (1H, d, 7.2, 2-H), 5.66 (1H, d, 5.1, 2'-H), 5.95 (1H, dd, 7.0, 5.1, 3'-H), 6.16 (1H, br.t, 8.0, 13-H), 6.28 (1H, s, 10-H), 7.24–7.90 (18H, m, NBz+OBz(meta, para)+3'-Ph+NH+Ar-H×4), 8.11 (2H, d, 7.1, OBz (ortho)).

c. 2'-(4-sulfobenzoyl) taxol, sodium salt. The tetrabutylammonium salt of 2'-(4-sulfobenzoyl)taxol was stirred with Dowex-50 ion exchange resin (Na+form, 2 ml) and H$_2$O (2 ml) for 1.5 h at rt, and the solution was then filtered through a small column (2 ml of same resin), and washed with H$_2$O (4×5 ml). The filtrate and washings were evaporated to dryness (<35° C., in vacuo) as an azeotrope with MeCN (10×4 ml) to yield the sodium salt of 2'-(4-sulfobenzoyltaxol) (12) (129.6 mg, 86%). Mp 230°–231° C. (MeOH). FAB-MS: m/z 1082 [M+Na]$^+$, 1060 [M+1]$^+$; $^1$H-NMR (CD$_3$OD, 270 MHz): 1.13 (6H, s, 16-CH $_3$+17-CH$_3$), 1.65 (3H, s, 19-CH$_3$), 1.96 (3H, s, 18-CH$_3$), 2.16 (3H, s, 10-OAc), 2.43 (3H, s, 4-OAc), 3.84 (1H, d, 7.0, 3-H), 4.18 (2H, s, 20-H), 4.36 (1H, dd, 10.3, 7.0, 7-H), 5.00 (1H, br.d, 8.0, 5-H), 5.63 (1H, d, 7.0, 2-H), 5.66 (1H, d, 7.4, 2'-H), 6.03 (1H, d, 6.4, 3'-H), 6.08 (1H, br.t, 9.0, 13-H), 6.46 (1H, s, 10-H), 7.29–7.68 (12H, m, NBz (meta,para)+OBz (meta,para))+NH+3'-Ph), 7.81 (2H, d, 7.0 NBz(ortho)), 7.92 (2H, d, 8.4, Ar-Hx2), 8.07 (2H, d, 8.4, Ar-Hx2), 8.16 (2H, d, 8.3, OBz (ortho)).

2'-[4-[2-(N,N-diethylamino)ethyl]aminocarbonyl]-benzoyl]taxol, HCl salt (13b).

a. 4-([2-(N,N-diethylamino)ethyl]aminocarbonyl)-benzoic acid was prepared from 4-benzyloxycarbonylbenzoic acid by reaction with N,N-diethylethylene diamine to yield the mono amide derivative which was hydrogenolysed to give the acid (CI-MS: m/z 265 [M+b]$^+$).

b. 2'-[4-([2-(N,N-diethylamino)ethyl]aminocarbonyl) benzoyl]taxol(13a). To a solution of the mono amide (58.0 mg, 0.22 mmol) in dry CH$_2$Cl$_2$ (20 ml), was added DCC (412.0 mg, 2 mmol), and 4-DMAP (49.0 mg, 0.4 mmol), the solution was stirred at room temperature for 0.5 h, then taxol (171.0 mg, 0.2 mmol) was added. The mixture was stirred at room temperature for 25h and filtered through Celite, and the filtrate evaporated to dryness (<35° C., in vacuo). CH$_2$Cl$_2$ (2 ml) was added to the residue, which was then eluted from Sephadex LH-20 (5g). The fractions eluted with 100% CH$_2$Cl$_2$ gave 13a (159.8 mg, 80%). Mp 184°–185° C. (H$_2$O). FAB/MS: m/z 1100 [M+1]$^+$, 532, $^1$H-NMR (CDCl$_3$, 270 MHz): 1.05 (6H, t, NCH$_2$CH$_3$×2), 1.13 (3H, s, 16-CH$_3$), 1.23 (3H, s, 17-CH$_3$), 1.68 (3H, s, 19-CH$_3$), 1.97 (3H, s, 18-CH$_3$), 2.23 (3H, s, 10-OAc), 2.44 (3H, s, 4-OAc), 2.59 (4H, dd, 7.3, 7.3, NCH$_2$CH$_3$×2), 2.68 (2H, t, 5.5, NHCH$_2$CH$_2$N), 3.50 (2H, dd, 5.5, 5.5, HNCH$_2$CH$_2$N), 3.81 (1H, d. 7.0, 3-H), 4.19 (1H, d, 8.4, 20-H), 4.31 (1H, d, 8.4, 20-H), 4.44 (1H, dd, 10.5, 6.4, 7-H), 4.97 (1H, br.d, 7.7, 5-H), 5.68 (1H, d, 7.0, 2-H), 5.69 (1H, d, 3.9, 2'-H), 6.06 (1H, dd, 9.0, 3.8, 3'-H), 6.26 (1H, br.t, 8.6, 13-H), 6.30 (1H, s, 10-H), 7.05 (1H, d, 9.0, NH), 7.26 (1H, br.s, NH), 7.26–7.70 (11H, m, NBz (meta, para)+OBz (meta, para)+3'Ph), 7.75 (2H, d, 7.0 NBz(ortho)), 7.86 (2H, d, 8.4, Ar-Hx2), 8.05 (2H, d, 8.4, Ar-Hx2), 8.12 (2H, d, 7.1, OBz (ortho)).

c. 2'-[4-([2-(N,N-diethylamino) ethyl ]aminocarbonyl) benzoyl]taxol, hydrochloride (13b). To a solution of 13a (148.6 mg, 0.135 mmol) in EtOH (2.8 ml), was added an HCl solution (1.17 ml, 0.135 mmol), the solution stirred for 0.5 h at room temperature then evaporated to a gummy solid (<35° C., in vacuo). $H_2O$ (2.8 ml), was added, the solution sonicated, then freeze-dried to yield 13b (153.1 mg, 99.7%). Mp 206°–207° C. ($H_2O$). FAB-MS: m/z 1100 [M+1-HCl]+, 429; $^1$H-NMR ($CDCl_3$, 270 MHz): 1.14 (3H, s, 16-$CH_3$), 1.23 (3H, s, 17-$CH_3$), 1.42 (6H, t, 7.1 ($NCH_2CH_3 \times 2$), 1.68 (3H, s, 19-$CH_3$), 1.98 (3H, s, 18-$CH_3$), 2.24 (3H, s, 10-OAc), 2.47 (3H, s, 4-OAc), 3.17 (4H, br.s, $NCH_2CH_3 \times 2$), 3.24 (2H, br.s, $HNCH_2CH_2N$), 3.83 (1H, d, 7.1, 3-H), 3.88 (2H, br.s, $HNCH_2CH_2N$), 4.20 (1H, d, 8.2, 20-H), 4.32 (1H, d, 8.2, 20'-H), 4.46 (1H, dd, 10.8, 6.7, 7-H), 4.98 (br.d, 8.5, 5-H), 5.68 (1H, d, 7.1, 2-H), 5.71 (1H, d, 3.6, 2'-H), 6.08 (1H, dd, 9.0, 3.6, 3'-H), 6.27 (1H, t, 9.0, 13-H), 6.31 (1H, s, 10-H), 7.19 (1H, d, 9.0, N}[), 7.26–7.70 (11H, m, NBz(meta,para)+OBz (meta,para)+3'Ph), 7.78 (2H, d, 7.4, NBz (ortho)), 8.05 (2H, d, 8.3, ArHzx2), 8.12 (2H, d, 8.3, Ar-Hx2), 8.17 (2H, d, 8.3, OBz(ortho)).

Taxol 2',7-di (sodium 1,2-benzenedicarboxylate) (15).

a. Taxol 2',7-di(hydrogen 1,2-benzene dicarboxylate) (14). To a solution of phthalic anhydride (124.3 mg, 0.84 mmol) in dry pyridine (6ml) with stirring at room temperature, was added taxol (50.0 mg, 0.059 mmol) and the solution stirred at room temperature for 17 h. The solution was evaporated to dryness (<35° C. in vacuo), and the residue purified by partition and Sephadex LH-20 elution as described for compound 3 to yield 14 (40.0 mg, 70%): mp 152°–153° C. (MeOH). FAB-MS: m/z 1172 [M+Na]+, 1150 [M+1]+; $^1$H-NMR ($CDCl_3$, 270 MHz): 1.17 (3H, s, 16-$CH_3$), 1.19 (3H, s, 17-$CH_3$), 1.26 (3H, s, 19-$CH_3$), 1.86 (3H, s, 18-$CH_3$), 2.05 (3H, s, 10-OAc), 2.45 (3H, s, 4-OAc), 4.01 (1H, d, 7.0, 3-H), 4.23 (1H, d, 7.1, 20-H), 4.33 (1H, d, 7.1, 20'-H), 5.12 (1H, br.d, 9.0, 5-H), 5.71 (1H, d, 7.0, 2-H), 5.86 (2H, m, 7-H+2'H), 6.00 (1H, m, 3'-H), 6.15 (1H, m, 13-H), 6.48 (1H, s, 10-H), 7.2–8.2 (24H, m, NBz+OBz+NH+3'Ph+ArH*8).

b. Taxol 2',7-di(sodium 1,2-benzenedicarboxylate) (15). To a solution of 14 (50.4 mg, 0.044 mmol) in acetone (0.5 ml), 0.4 ml of a solution of $NaHCO_3$ (7.38 mg, 0.088 mmol) in $H_2O$ was added. The solution was evaporated to a gummy solid in vacuo (35° C. 1.0 ml of $H_2O$ was added and sonicated, and the solution freeze-dried to dryness to yield 15 (49.3 mg, 94%): mp 219°—219° C. (MeOH). FAB-MS: m/z 1191 [M-2]+, 1170 [M-Na]+, 1150 [M-2Na+2+1]+, 1023 [M-$OCC_4H_6COONa$)+1]+; $^1$H-NMR (($CD_3$)$_2$CO, 270 MHz): 1.17 (3H, s, 16-$CH_3$), 1.20 (3H, 2, 17-$CH_3$), 1.25 (3H, s, 19-$CH_3$), 1.80 (3H, s, 18-$CH_3$), 2.00 (3H, s, 10-OAc), 2.33 (3H, s, 4-OAc), 3.85 (1H, d, 7.0, 3-H), 4.15 (1H, d, 8.8, 20-H), 4.26 (1H, d, 8.8, 20-H), 4.82 (1H, d, 8.3, 5-H), 5.52 (1H, br.s, 2'-H), 5.63 (1H, m, 3'-H), 5.66 (1H, d, 7.0, 2-H), 5.85 (1H, m, 13-H), 6.36 (1H, s, 10-H), 7.16–8.07 (24H, m, Ar-H*23+NH).

Taxol 2',7-di(sodium 1,4-benzenedicarboxylate) (17)

a. To a solution of 4-benzyloxycarbonylbenzoic acid (45.1 mg, 0.176 mmol) in dry $CH_2Cl_2$ (5 ml) was added DCC (120.7 mg, 0.59 mmol) and 4-DMAP (14.3 mg, 0.117 mmol), the solution stirred at room temperature for 0.5 h, then taxol (50.0 mg, 0.059 mmol) was added.

The solution was stirred at room temperature for 23 h, and worked up as described previously. The crude product was purified by PTLC ($SiO_2$, $CH_2Cl_2$:MeOH, 95:5) to yield three compounds: 2'7-di-(4-benzyloxocarbonylbenzoyl) taxol (16) (46.1 mg, 59.2%), 2'-(4-benzyloxocarbonylbensoyl -7-(4-carboxybensoyl)taxol (17) (9.1 mg, 12.5%), and 2'(4-benzyloxocarbonylbensoyl)-taxol (5) (12.6 mg, 19.7%).

Compound 16: $^1$H-NMR ($CDCl_3$, 270 MHz): 1.17 (3H, s, 16-$CH_3$), 1.20 (3H, s, 17-$CH_3$), 1.94 (3H, s, 19-$CH_3$), 2.05 (3H, s, 18-$Ch_3$), 2.17 (3H, s, 10-OAc), 2.47 (3H, s, 4-OAc), 4.05 (1H, d, 6.8, 3-H), 4.40 (1H, d, 8.3, 20-H), 4.36 (1H, d, 8.3, 20'-H), 5.01 (1H, d, 8.4, 5-H), 5.39 (4H, br.s, 2*$OCCH_2Ph$), 5.72 (1H, d, 4.0, 2'-H), 5.74 (1H, d, 6.8, 2-H), 5.78 (1H, dd, 9.0, 7.0, 7-H), 6.06 (1H, dd, 9.0, 4.0, 3'-H), 6.26 (1H, t, 8.1, 13-H), 6.37 (1H, s, 10-H), 6.99 (1H, d, 9.0, NH), 7.26–7.52 (21H, m, NBz (meta,para)+OBz (meta,para)+3'-Ph+Bn*2)), 7.77 (2H, d, 7.3, NBz (ortho)), 7.97 (2H, d, 8.3, At-H*2), 8.04 (2H, d, 8.3, ArH*2), 8.11 (2H, d, 8.3, ArH*2), 9.13 (2H, d, 8.0, OBz (ortho)), 8.16 (2H, d, 8.3, Ar-H*2).

b. Taxol 2',7-di(hydrogen 1,4-benzenedicarboxylate) (18). To a solution of 16 (44.1 mg, 0.033 mmol) in AcOEt (1.0 ml) was added Pd/C (10%, 6.6 mg) and 2 drops of AcOH, and the solution stirred under Hz at room temperature for 12 h and then filtered. The filtrate was evaporated to dryness (in vacuo, <30° C.) to yield 18 (36.3 mg, 95.2%). Compound 18 (8.0 mg, 94%) was also obtained from compound 17 by a similar procedure.

Compound 18: FAB-MS m/z: 1172 [M+Na]+, 1150 [M+1]+; $^1$H-NMR (($CD_3$)$_2$CO, 270 MHz): 1.20 (6H, s, 16-$CH_3$+17-$CH_3$), 1.93 (3H, s, 19-$CH_3$), 1.96 (3H, s, 18-$CH_3$), 2.07 (3H, s, 10-OAc), 2.55 (3H, s, 4-OAc), 4.07 (1H, d, 7.0, 3-H), 4.25 (2H, s, 20-H), 5.07 (1H, br.d, 8.3, 5-H), 5.76 (1H, d, 7.0 2-H), 5.78 (1H, d, 7.1, 2'-H), 5.85 (1H, dd, 10.3, 7.2, 7-H), 6.18 (2H, m, 13-H+3'-H), 6.42 (1H, s, 10-H), 7.34–8.26 (24 H, m, ArH*24), 8.69 (1H, d, 8.0, COOH).

c. Taxol 2',7-di(sodium 1,4-benzenedicarboxylate) (19). To a solution of 18 (36.3 mg, 0.0316 mmol) in acetone (0.5 mmol), 0.2 ml of a solution of $NaHCO_3$ (5.31 mg, 0.0632 mmol) in $H_2O$ was added and the solution evaporated to a gummy solid (<30° C. in vacuo). The solid was dissolved in $H_2O$ (1 ml), sonicated, and freeze-dried to yield 19 (37.7 mg, 99.9%): mp 244°–245° C. (MeOH). FAB-MS: m/z 1191 [M-2]+, 1170 [M-Na]+, 1023 (M-($OCC_6H_4COONa$)+1]+; $^1$H-NMR ($CD_3OD$, 270 MHz): 1.13 (6H, br.d, 16-$CH_3$+17-$CH_3$), 1.92 (6H, br.s, 19-$CH_3$+18-$CH_3$), 1.99 (3H, s, 10-OAc), 2.48 (3H, s, 4-OAc), 4.04 (1H, d, 7.7, 3-H), 4.24 (2H, br.s, 20-H), 5.06 (1H, br.d, 7.0, 5-H), 5.65 (1H, d, 7.6, 2'-H), 5.71 (1H, d, 7.7, 2-H), 5.81 (1H, m, 7-H), 6.05 (1H, d, br.d, 7.6, 3'-H), 6.12 (1H, t, 9..0, 13-H), 6.42 (1H, s, 10-H), 7.20–8.20 (24H, m, NBz+OBz+3'-Ph+NH+Ar-H*8).

SOLUBILITY AND STABILITY

Solubility and stability values for compounds of the present invention are shown in Table 1. All of the compounds in Table 1 are stable in mildly acidic aqueous solution for more than 24 hours, and they all exhibit enhanced water solubility relative to taxol. In separate experiments, taxol derivative 4 and 2'-succinyl taxol (R=$NaO_2CCH_2CH_2CO_2$) were dissolved in a mildly basic aqueous solution. The solution containing 2'-succinyl taxol turned cloudy in less than 24 hours, while the solution containing the 2'-0-benzoyl derivative 4 remained clear. The 2'-succinyl taxol was about 50% decomposed while 4 remained substantially intact. Thus, it was demonstrated that under some conditions (e.g. mild base), 2'-0-benzoyl derivatives are more stable than 2'-aliphatic derivatives.

It has surprisingly been found that the parabenzoyl carboxylate derivate 7 is twice as soluble as the ortho benzoyl carboxylate derivative 4. The trisodium derivative 9b was astonishingly found to be more than 1500 times more water soluble than taxol (see Table 1).

TABLE 1
SOLUBILITY AND STABILITY OF SOME WATER-SOLUBLE DERIVATIVES OF TAXOL

| No. | 2'-(R) Taxol R = | Relative Solubility (p')* | Stabilities at pH 5** |
|---|---|---|---|
| Taxol | —OH | 1 | |
| 4 | o-NaO$_2$C—C$_6$H$_4$—CO$_2$— | 3 | >24h (a) |
| 7 | p-NaO$_2$C—C$_6$H$_4$—CO$_2$— | 6 | >24h (a) |
| 8c | 3,5-di-NaO$_2$C—C$_6$H$_4$—CO$_2$— | 455 | >24h (b) |
| 9b | 2,4,5-tri-NaO$_2$C—C$_6$H$_4$—CO$_2$— | 1573 (c) | >24h (b) |
| 11 | o-NaO$_3$S—C$_6$H$_4$—CO2 | 96 | >24h (b) |
| 12 | p-NaO$_3$S—C$_6$H$_4$—CO2 | 166 | >24h (b) |
| 13b | HCl*p-(CH$_3$CH$_2$)$_2$NCH$_2$—CH$_2$NHOC—C$_6$H$_4$—CO$_2$ | 7 | >24h (a) |
| | —O$_2$CCH$_2$CH$_2$SO$_3$Na (d) | 477 | >24h (b) |
| | —O$_2$CCH$_2$CH$_2$CONHCH$_2$—CH$_2$SO$_3$Na (e) | 421 | >24h (b) |

*Solubilities were determined by using the 1-octanol and water partition method. Sample concentrations in water were determined by UV absorptions at 228 nm.
**Stabilities were determined in pH 5 buffer solution by one of the two methods indicated below.
(a) 9.5 mg of sample was dissolved in 0.2 ml of EtOH and 0.2 ml of pH 5 buffer solution and let stand at room temperature. The progress of decomposition was checked by HPLC or TLC and observation of the onset of cloudiness.
(b) 0.5 mg of sample was dissolved in 0.1 ml of EtOH and 0.9 ml of pH 5 buffer solution, the other conditions were the same as in (a) above. All samples were stable under these conditions for at least 24 hours. No hydrolysis was detectable by HPLC or TLC during this time period.
(c) The solubility of the compound in pure water is >227 mg/ml.
(d) This compound was first prepared by Zhao et al, J. Nat. Prod., 54, 1607-1611, 1991, using Michael addition. It was reprepared on a 200 mg scale, using a different synthetic pathway via sulfopropionic acid anhydride.
(e) This compound was first prepared by Zhao et al. It was reprepared on a 200 mg scale and for comparison with earlier data.

Biological Evaluation

Balb/o x DBA/2 F1 hybrid mice were implanted intraperitoneally, as described by William Rose in "Evaluation of Madison 109 Lung Carcinoma as a Model for Screening Antitumor Drugs, "Cancer Treatment Reports, 65 No. 3-4 (1981), with 0.5 mL of a 2% (w/v) brei of M109 lung carcinoma (the mice M109 model).

Mice were treated with a compound under study by receiving intraperitoneal injections of various doses on either Day 1, 5, and 9 post-tumor implant or Days 5 and 8 post-implant. Mice were followed daily for survival until approximately 75-90 days post-tumor implant. One group of mice per experiment remained untreated and served as the control group.

Median survival times of compound-treated (T) mice were compared to the median survival time of the control (C) mice. The ratio of the two values for each compound-treated group of mice was multiplied by 100 and expressed as a percentage (i.e.% T/C) in Table 2 for certain representative compounds.

All of the tested compounds exhibited some biological activity. It is particularly important to note that the parabenzoyl carboxylate derivative 7 exhibits superior in vivo biological activity relative to the ortho benzoyl carboxylate derivative 4 (see Table 2).

TABLE 2
IN VIVO ACTIVITY OF TAXOL PRODRUGS

| Compound # | Schedule, site route | Dose | T/C |
|---|---|---|---|
| 4 | Q03Dx2;5 ip/ip | 60 | 141 |
| | | 30 | 135 |
| | | 15 | 106 |
| 7 | Q03Dx2;5 ip/ip | 60 | 141 |
| | | 30 | 141 |
| | | 15 | 112 |
| 13b | Z03Dx2;5 ip/ip | 200 | 124 |
| | | 100 | 118 |
| | | 50 | 118 |
| 15 | Z03Dx2;5 | 60 | 106 |
| | | 30 | 103 |
| | | 15 | 100 |
| 17 | Q03Dx2;5 ip/ip | 52 | 109 |
| | | 26 | 100 |
| | | 13 | 97 |

The present invention discloses a general method for preparing derivatives of taxol congeners having an 0-aroyl group at the C-2' position and derivatives of taxol congeners with 0-aroyl groups at the C-2' and C-7 positions wherein at least one of the aroyl moieties on the taxol congener has at least one substituent selected from the group consisting of alkyls, aryls, esters, SO$_3^-$X$^+$, COO$^-$X$^+$, and ammonio cations, wherein X$^+$ is any suitable counter ion and further wherein the aroyl is not 1,2 benzene dicarboxylate.

From the above teachings it is apparent that many modifications and variations of the present invention are possible. It is therefore to be understood that the invention may be practiced otherwise than specifically described. By way of non-limiting example, the N-acyl derivatives of taxol and 7-epi taxol could be used in place of taxol in the present invention, in order to obtain taxol derivatives for use as commercial standards or for use as anticancer agents.

We claim:

1. Taxol congeners having the taxane tetracyclic nucleus and C-13 side-chain of Formula I wherein R is selected from the group consisting of aryl, alkoxy, alkyl, and alkenyl, and the C-1, C-2 and C-4 positions have the same substituents as in taxol and wherein the C-7 position has a substituent selected from the group consisting of hydroxy, triethylsilyloxy, and ester and the C-10 position has a substituent selected from the group consisting of hydroxy and ester; and having a C-2'-0-aroyl substituent wherein said aroyl substituent has at least two substituents independently selected from the group consisting of alkyl, aryl, ester, sulfonate, carboxylate, and ammonio cation and wherein the Formula I is as follows:

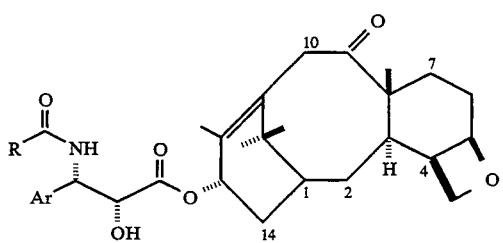

2. Compounds of claim 1 having the following structure:

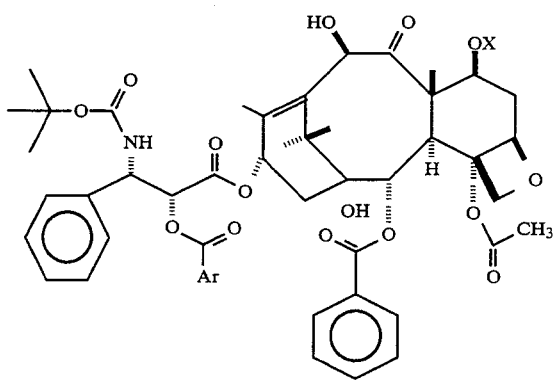

wherein said aroyl substituent, ArC(O), is a benzoyl substituent having the structure:

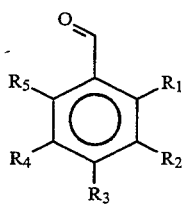

wherein $R_1$, $R_2$, $R_3$, $R_4$ and $R_5$ are independently selected from the group consisting of H, alkyl, aryl, ester, sulfonate, carboxylate and ammonio cation; provided that at least two of $R_1$–$R_5$ are independently selected from the group consisting of sulfonate, carboxylate, ammonio cation, alkyl containing a substituent selected from the group consisting of sulfonate, carboxylate, and ammonio cation, and aryl containing a substituent selected from the group consisting of sulfonate, carboxylate and ammonio cation and X is selected from the group consisting of H, $Si(C_2H_5)_3$, and aroyl.

3. Compounds of claim 1 having the following structure:

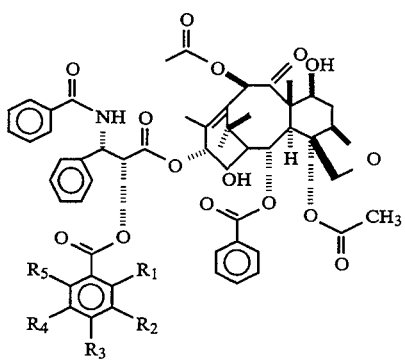

wherein:

$R_1$, $R_2$, $R_3$, $R_4$ and $R_5$ are independently selected from the group consisting of H, alkyl, aryl, ester, $SO_3^-X^+$, $COO^-X^+$, and ammonio cation, provided that at least two of $R_1$–$R_5$ are independently selected from the group consisting of alkyl, aryl, ester, $SO_3^-X^+$, $COO^-X^+$, and ammonio cation, and wherein $X^+$ is selected from the group consisting of $H^+$, the alkali metal cations, and the ammonio cations.

4. Compounds of claim 3, wherein at least one of $R_2$, $R_3$, or $R_4$ is selected from the group consisting of $SO_3^{-X+}$, $COO^-X^+$, ammonio cation, alkyl containing a substituent selected from the group consisting of $SO_3^-X^+$, $COO^-X^+$, and ammonio cation, and aryl containing a substituent selected from the group consisting of $SO_3^-X^+$, $COO^-X^+$, and ammonio cation.

5. Compounds of claim 3, wherein at least two of $R_1$–$R_5$ are independently selected from the group consisting of sulfonate, carboxylate, ammonio cation, alkyl containing a substituent selected from the group consisting of $SO_3^-X^+$, $COO^-X^+$, and ammonio cation, and aryl containing a substituent selected from the group consisting of $SO_3^-X^+$, $COO^-X^+$, and ammonio cation.

6. Compounds of claim 3, wherein $X^+$ is selected from the group consisting of the alkali metal cations, and the ammonio cations.

7. Compounds of claim 5, wherein X is selected from the group consisting of Na, K, $N(CH_3)_4$, $N(CH_2CH_3)_4$, $N[(CH_2)_2CH_3]_4$, $N[(CH_2)_3CH_3)]$, $N[(CH_2)_4CH_3]_4$, and $N[(CH_2)_5CH_3]_4$.

8. Compounds of claim 6, wherein X is Na.

9. Compounds of claim 3, wherein:

$R_1$, $R_2$, $R_4$, and $R_5$ are all H and $R_3$ is selected from the group consisting of $SO_3^-X^+$, [$COO^-X^+$,] ammonio cation, alkyl containing a substituent selected from the group consisting of $SO_3^-X^+$, $COO^-X^+$, and ammonio cation, and aryl containing a moiety selected from the group consisting of $SO_3^-X^+$, $COO^-X^+$, and ammonio cation.

10. The compound of claim 3, wherein:

$R_1$, $R_3$ and $R_5$ are H and $R_2$ and $R_4$ are $COO^-Na^+$.

11. The compound of claim 3, wherein:

$R_2$ and $R_5$ are H and $R_1$, $R_3$, and $R_4$ are $COO^-Na^+$.

12. Compounds of claim 3, wherein:

$R_3$ is $C(O)NHCH_2CH_2$ $NR_aR_bHY$ wherein $R_a$ and $R_b$ are independently selected from the group consisting of the aryls and lower alkyls and Y is a halogen.

13. The compound of claim 12 wherein $R_1$, $R_2$, $R_4$ and $R_5$ are all H, Y is Cl, and $R_a$ and $R_b$ are $C_2H_5$.

14. A pharmaceutical composition comprising an antineoplastically effective amount of at least one of the compounds of claim 1 and a pharmaceutically effective excipient.

15. A method for treating ovarian or breast cancer comprising the administration of an antineoplastically effective amount of the compound of claim 3.

16. Taxol compounds having the following structure:

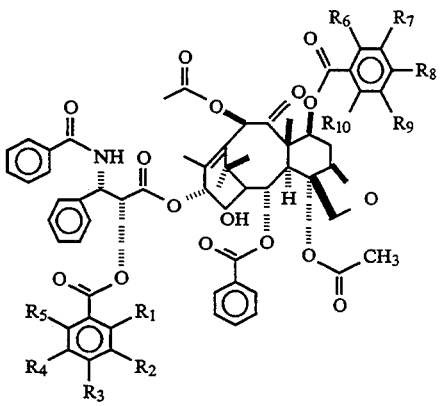

wherein $R_1$–$R_{10}$ are independently selected from the group consisting of H, alkyl, aryl, ester, $SO_3^-X^+$, $COO^-X^+$, and ammonio cation, wherein $X^+$ is selected from the group consisting of $H^+$, the alkali metal cations, and the ammonio cations.

17. Compounds of claim 16, wherein at least one of $R_1$–$R_{10}$ is selected from the group consisting of $SO_3^-X^+$, and $COO^-X^+$.

18. Compounds of claim 16, wherein $R_2$–$R_5$ and $R_7$–$R_{10}$ are H, $R_1$ is the same as $R_6$, and $R_1$ is selected from the group consisting of COOH and COONa.

19. Compounds of claim 16, wherein at least one of $R_1$–$R_{10}$ is selected from the group consisting of sulfonate, carboxylate, ammonio cation, alkyl containing a substituent selected from the group consisting of $SO_3^-X^+$, $COO^-X^+$, and ammonio cation, and aryl containing a substituent selected from the group consisting of $SO_3^-X^+$, $COO^-X^+$, and ammonio cation.

20. Compounds of claim 16, wherein $R_1$–$R_{10}$ are independently selected from the group consisting of H, $SO_3^-X^+$, $COO^-X^+$, and esters.

21. The compound of claim 20 wherein $R_1$, $R_2$, $R_4$, $R_5$, $R_6$, $R_7$, $R_9$, and $R_{10}$ are all H; and $R_3$ and $R_8$ are selected from the group consisting of COOH, COONa and $COOCH_2Ph$.

22. A pharmaceutical composition comprising an antineoplastically effective amount of at least one of the compounds of claim 19 as an active ingredient.

23. Compounds of claim 1 wherein aroyl is benzoyl.

24. Compounds of claim 23 wherein sulfonate has the formula $SO_3^-X^+$ and carboxylate has the formula $COO^-X^+$, wherein $X^+$ is selected from the group consisting of $H^+$, the alkali metal cations, and the ammonio cations.

25. Compounds of claim 24 wherein said benzoyl substituent has at least two carboxylate substituents.

26. Compounds of claim 24 wherein the substituents on said benzoyl substituent are independently selected from the group consisting of H, alkyl, aryl, ester, $SO_3^-X^+$, $COO^-X^+$, and ammonio cation provided that at least two of $R_1$–$R_5$ are independently selected from the group consisting of alkyl, aryl, ester, $SO_3^-X^+$, $COO^-X^+$, and ammonio cation, and wherein $X^+$ is selected from the group consisting of $H^+$, the alkali metal cations, and the ammonio cations.

27. Compounds of claim 3 wherein at least two of $R_1$–$R_5$ are $COO^-X^+$.

28. Compounds of claim 27 wherein $X^+$ is $Na^+$.

29. Taxol congeners having the taxane tetracyclic nucleus and C-13 side-chain of Formula I, wherein R is selected from the group consisting of aryl, alkoxy, alkyl, and alkenyl, and the C-1, C-2 and C-4 positions have the same substituents as in taxol and wherein the C-7 position has a substituent selected from the group consisting of hydroxy, triethylsilyloxy, and ester and the C-10 position has a substituent selected from the group consisting of hydroxy and ester: and having a C-2'-O-aroyl substituent, wherein the aroyl substituent has at least one substituent selected from the group consisting of alkyl, aryl, ester and sulfonate and wherein the Formula I is as follows:

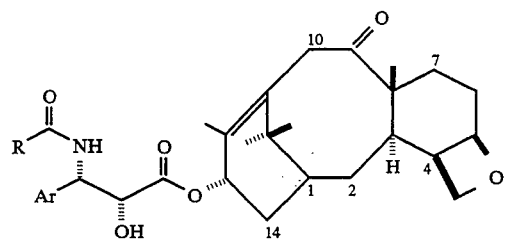

30. Compounds of claim 29 having the following structure:

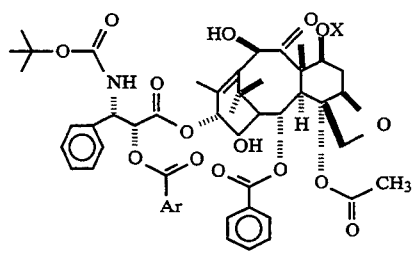

wherein said aroyl substituent, ArC(O), is a benzoyl substituent, having the structure:

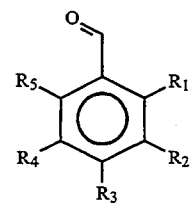

wherein $R_1$, $R_2$, $R_3$, $R_4$ and $R_5$ are independently selected from the group consisting of H, alkyl, aryl, ester, sulfonate, carboxylate and ammonio cation; provided that at least two of $R_1$–$R_5$ are independently selected from the group consisting of sulfonate, carbonate, ammonio cation, alkyl containing a substituent selected from the group consisting of sulfonate, carbonate, and ammonio cation, and aryl containing a substituent selected from the group consisting of sulfonate, carbonate and ammonio cation and X is selected from the group consisting of H, $Si(C_2H_5)_3$, and aroyl.

31. Compounds of claim 29 having the following structure:

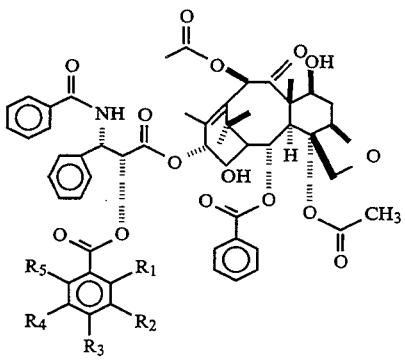

wherein:

R₁, R₂, R₃, R₄ and R₅ are independently selected from the group consisting of H, alkyl, aryl, ester, and $SO_3^-X^+$, wherein $X^+$ is selected from the group consisting of $H^+$, the alkali metal cations and the ammonio cations.

32. Compounds of claim 31, wherein at least one of R₁–R₅ is selected from the group consisting of sulfonate, carboxylate, ammonio cation, alkyl containing a substituent selected from the group consisting of $SO_3^-X^+$, $COO^-X^+$, and ammonio cation, and aryl containing a substituent selected from the group consisting of $SO_3^-X^+$, $COO^-X^+$, and ammonio cation.

33. Compounds of claim 31, wherein $X^+$ is selected from the group consisting of the alkali metal cations, and the ammonio cations.

34. Compounds of claim 31, wherein X is selected from the group consisting of Na, K, $N(CH_3)_4$, $N(CH_2CH_3)_4$, $N[(CH_2)_2CH_3]_4$, $N[(CH_2)_3CH_3)]$, $N[(CH_2)_4CH_3]_4$, and $N[(CH_2)_5CH_3]_4$.

35. Compounds of claim 34, wherein X is Na.

36. Compounds of claim 35, wherein:

R₁, R₂, R₄ and R₅ are all H and R₃ is selected from the group consisting of $SO_3^-X^+$, alkyl containing a substituent selected from the group consisting of $SO_3^-X^+$, $COO^-X^+$, and ammonio cation, and aryl containing a substituent selected from the group consisting of $SO_3^-X^+$, $COO^-X^+$, and ammonio cation.

37. The compound of claim 31, wherein:

R₂, R₃, R₄, and R₅ are all H and R₁ is $SO_3^-X^+$.

38. A pharmaceutical composition, comprising an antineoplastically effective amount of at least one of the compounds of claim 29 and a pharmaceutically effective excipient.

39. Taxol congeners having the taxane tetracyclic nucleus and C-13 side-chain of Formula I, wherein R is selected from the group consisting of aryl, alkoxy, alkyl, and alkenyl, and the C-1, C-2 and C-4 positions have the same substituents as in taxol and wherein the C-7 position has a substituent selected from the group consisting of hydroxy, triethylsilyloxy, and ester and the C-10 position has a substituent selected from the group consisting of hydroxy and ester; and having an 0-benzoyl substituent at the C-2' position, wherein the benzoyl substituent has the general formula:

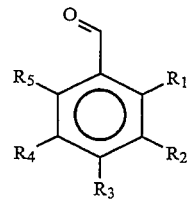

wherein R₃ is selected from the group consisting of $COO^-X^+$, $SO_3^-X^-$, alkyl containing a substituent selected from the group consisting of $SO_3^-X^+$, $COO^-X^+$, and ammonio cation, and aryl containing a substituent selected from the group consisting of $SO_3^-X^+$, $COO^-X^+$, and ammonio cation; wherein $X^+$ is selected from the group consisting of the alkali metal cations and the ammonio cations; and wherein R₁, R₂, R₄, and R₅ are independently selected from the group consisting of H, alkyl, aryl, ester, sulfonate, carbonate, and ammonio cation and wherein the Formula I is as follows:

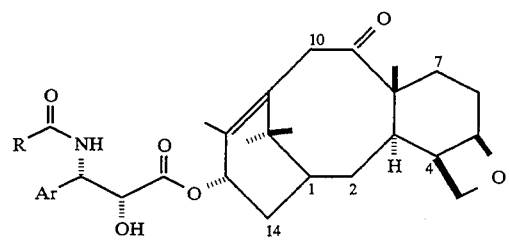

40. Compounds of claim 39 having the following structure:

wherein:
said aroyl substituent, ArC(O), is a benzoyl substituent, having the structure:

wherein R₁, R₂, R₄ and R₅ are independently selected from the group consisting of H, alkyl, aryl, ester, sulfonate, carboxylate and ammonio cation; provided that R₃ is independently selected from the group consisting of sulfonate, carbonate, ammonio cation, alkyl containing a substituent selected from the group consisting of sulfonate, carbonate, and ammonio cation, and aryl containing a substituent selected from the group consisting of sulfonate, carbonate and ammonio cation and X is selected from the group consisting of H, Si(C$_2$H$_5$)$_3$, and benzoyl.

41. Compounds of claim 39 having the following structure:

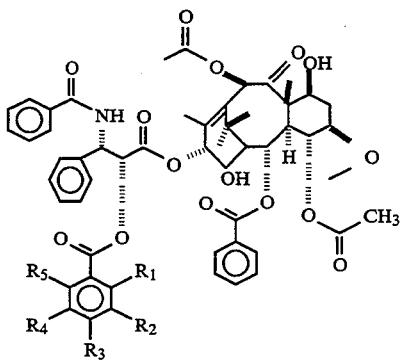

wherein:

R$_1$, R$_2$, R$_4$ and R$_5$ are independently selected from the group consisting of H, alkyl, aryl, ester, SO$_3^-$X$^+$, COO$^-$X$^+$, and ammonio cation; wherein X$^+$ is selected from the group consisting of H$^+$, the alkali metal cations and the ammonio cations.

42. Compounds of claim 31, wherein at least one of R$_2$, R$_3$, or R$_4$ is selected from the group consisting of SO$_3^-$X$^+$, ammonio cation, alkyl containing a substituent selected from the group consisting of SO$_3^-$X$^+$, COO$^-$X$^+$, and ammonio cation, and aryl containing a substituent selected from the group consisting of SO$_3^-$X$^+$, COO$^-$X$^+$, and ammonio cation.

43. Compounds of claim 39, wherein X is selected from the group consisting of Na, K, N(CH$_3$)$_4$, N(CH$_2$CH$_3$)$_4$, N((CH$_2$)$_2$CH$_3$)$_4$, N((CH$_2$)$_3$CH$_3$)$_4$, N((CH$_2$)$_4$CH$_3$)$_4$, and N((CH$_2$)$_5$CH$_3$)$_4$.

44. Compounds of claim 43, wherein:

R$_3$ is COO$^-$Na$^+$ and R$_1$, R$_2$, R$_4$ and R$_5$ are all hydrogen.

45. A pharmaceutical composition, comprising an antineoplastically effective amount of at least one of the compounds of claim 39 and a pharmaceutically effective excipient.

46. Taxol congeners having the taxane tetracyclic nucleus and C-13 side-chain of Formula I, wherein R is selected from the group consisting of aryl, alkoxy, alkyl, and alkenyl, and the C-1, C-2 and C-4 positions have the same substituents as in taxol and wherein the C-7 position has a substituent selected from the group consisting of hydroxy, triethylsilyloxy, and ester and the C-10 position has a substituent selected from the group consisting of hydroxy and ester: and having an 0-benzoyl substituent at the C-2' position wherein the benzoyl substituent has the general formula:

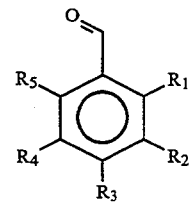

wherein R$_3$ is selected from the group consisting of COO$^-$X$^+$, SO$_3^-$X$^+$, alkyl containing a substituent selected from the group consisting of SO$_3^-$X$^+$, COO$^-$X$^+$, and ammonio cation, and aryl containing a substituent selected from the group consisting of SO$_3^-$X$^+$, COO$^-$X$^+$, and ammonio cation; wherein X$^+$ is H$^+$; and wherein R$_1$, R$_2$, R$_4$, and R$_5$ are independently selected from the group consisting of H, alkyl, aryl, ester, sulfonate, carbonate, and ammonio cation and further wherein said taxol congeners are intermediates that can be converted via cation exchange to congeners having increased water solubility relative to taxol and wherein the Formula I is as follows:

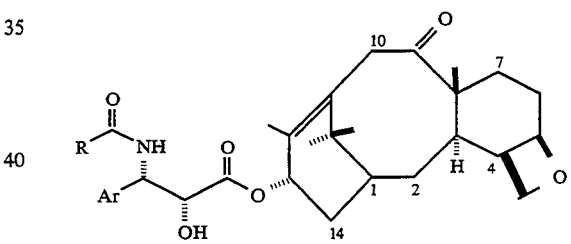

47. Compounds of claim 46, wherein R$_1$, R$_2$, R$_4$, and R$_5$ are H.

* * * * *